US012678386B2

(12) United States Patent
Cocito Armanino et al.

(10) Patent No.: US 12,678,386 B2
(45) Date of Patent: Jul. 14, 2026

(54) ORGANIC COMPOUNDS AS TRPM8 ACTIVATORS

(71) Applicant: Givaudan SA, Vernier (CH)

(72) Inventors: Nicolas Cocito Armanino, Baden (CH); Lijun Zhou, Shanghai (CN)

(73) Assignee: GIVAUDAN SA, Vernier (CH)

( * ) Notice: Subject to any disclaimer, the term of this patent is extended or adjusted under 35 U.S.C. 154(b) by 407 days.

(21) Appl. No.: 18/276,412

(22) PCT Filed: Feb. 9, 2022

(86) PCT No.: PCT/EP2022/053085
§ 371 (c)(1), (2) Date: Aug. 8, 2023

(87) PCT Pub. No.: WO2022/171653
PCT Pub. Date: Aug. 18, 2022

(65) Prior Publication Data

US 2024/0139087 A1 May 2, 2024

(30) Foreign Application Priority Data

Feb. 9, 2021 (WO) ................ PCT/CN2021/076366

(51) Int. Cl.

| | |
|---|---|
| ***A61K 8/49*** | (2006.01) |
| ***A61K 31/4178*** | (2006.01) |
| ***A61K 31/454*** | (2006.01) |

(52) U.S. Cl.
CPC .......... *A61K 8/494* (2013.01); *A61K 31/4178* (2013.01); *A61K 31/454* (2013.01); *A61K 2800/244* (2013.01)

(58) Field of Classification Search
CPC .. A61K 8/494; A61K 31/4178; A61K 31/457; A61K 2800/244
See application file for complete search history.

(56) References Cited

U.S. PATENT DOCUMENTS

| | | | | |
|---|---|---|---|---|
| 9,394,287 | B2 * | 7/2016 | Priest | A61K 8/494 |
| 2016/0317532 | A1 | 11/2016 | Priest et al. | |
| 2016/0339026 | A1 | 11/2016 | Noncovich et al. | |
| 2020/0190052 | A1 | 6/2020 | Join et al. | |

FOREIGN PATENT DOCUMENTS

| | | | |
|---|---|---|---|
| CN | 103201279 | A | 7/2013 |
| WO | 2012061698 | A2 | 5/2012 |
| WO | 2017058594 | A1 | 4/2017 |
| WO | 2019012071 | A1 | 1/2019 |
| WO | 2021074281 | A1 | 4/2021 |

OTHER PUBLICATIONS

International Search Report for Application No. PCT/CN2021/076366 dated Nov. 9, 2021.
International Written Opinion for Application No. PCT/CN2021/076366 dated Nov. 9, 2021.
International Search Report for Application No. PCT/EP2022/053085 dated May 3, 2022.
International Written Opinion for Application No. PCT/EP2022/053085 dated May 3, 2022.
Breslin, H.J. et al., “Rationale, Design, and Synthesis of Novel Phenyl Imidazoles as Opioid Receptor Agonists for Gastrointestinal Disorders”, J. Med. Chem., dated Sep. 4, 2004, pp. 5009-5020, vol. 47.
Noncovich, A. et al., “Discovery and development of a novel class of phenoxyacetyl amides as highly potent TRPM8 agonists for use as cooling agents”, Bioorganic & Medicinal Chemistry Letters, dated Apr. 11, 2017, Apr. 11, 2017, pp. 3931-3938, vol. 27.

* cited by examiner

*Primary Examiner* — Kamal A Saeed
(74) *Attorney, Agent, or Firm* — CURATOLO SIDOTI & TRILLIS CO., LPA; Floyd Trillis, III; Salvatore A. Sidoti

(57) ABSTRACT

Disclosed are TRPM8 modulators as defined by formula (I) for achieving a cooling effect on skin and mucousa.

14 Claims, No Drawings

ORGANIC COMPOUNDS AS TRPM8 ACTIVATORS

CROSS REFERENCE TO RELATED APPLICATIONS

This application is a national stage application of International Application No. PCT/EP2022/053085, filed 9 Feb. 2022, which claims priority from International Application No. PCT/CN2021/076366, filed 9 Feb. 2021, both of which applications are incorporated herein by reference.

TECHNICAL FIELD

The present invention relates to a particular class of compounds capable to activate TRPM8 ion channels. It further relates to the use of said compounds for inducing a sensation of coldness, and to consumer products comprising these compounds.

BACKGROUND

TRPM8 (transient receptor potential melastatin member 8, also known as Trp-p8 or MCR1) is activated by innocuous cool and thus plays an important role as sensor for temperature. The channels are widely distributed in different tissues (such as human skin and mucosa (such as oral mucosa, throat mucosa, and nasal mucosa), male urogenital tract, lung epithelium cells and artery myoctes). They are $Ca^{2+}$-permeable, nonselective cation channels that exhibit polymodal gating mechanisms, being activated by innocuous cool to cold temperature, membrane depolarization, and molecules which are known as cooling agents including natural and synthetic compounds. The receptor was described for the first time in 2002 as cold receptor in a number of publications.

The present invention is based on the finding that a particular class of compounds can be used to drive a cooling response when brought into contact with TRPM8 receptor in-vitro and in-vivo.

Compounds providing a cooling sensation have for a long time played an important role in the flavor and fragrance industry in order to produce an association with freshness and cleanliness. Cooling compounds are widely used in a variety of products such as foodstuffs, tobacco products, beverages, dentifrices, mouthwashes, toothpastes, and toiletries. The cooling sensation provided contributed to the appeal and acceptability of consumer products. In particular, oral care products, such as dentifrices and mouthwashes are formulated with coolants because they provide breath freshening effects and a clean, cool, fresh feeling in the mouth.

A large number of compounds providing cooling sensations have been described. The most well-known natural occurring compound is menthol, in particular L-menthol. Among the synthetic compounds providing cooling sensations, many are derivatives of or are structurally related to menthol, i. e. containing the cyclohexane moiety, and derivatized with functional groups including carboxamide, ketal, ester, ether and alcohols.

Applicant surprisingly found a new class of chemical compounds which differ significantly in structural terms from the TRPM8 modulators known hitherto. It was surprisingly found that this class of chemical compounds as herein further described can provide long lasting cooling on the human skin and/or mucosa at very low concentrations.

SUMMARY

There is provided in a first aspect a compound of formula (I), a salt or solvate thereof (in particular for use in providing cooling sensation)

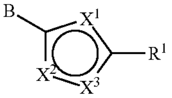

(I)

wherein one of $X^1$, $X^2$, and $X^3$ is >N—C(O)R and the other two are independently selected from C, N, and O, with the proviso that not both of them are C, and wherein R is selected from $C_1$-$C_{15}$ hydrocarbon residue optionally comprising one heteroatom selected from O and S; and a) $R^1$ is H; and B represents a monovalent residue (a)

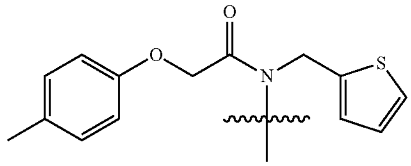

(a)

or b) $R^1$ is selected from halogen (including Br, Cl, and F), $C_6$-$C_{10}$ aryl (e.g. phenyl, or naphthyl) optionally substituted with up to four (e.g. 1, 2, or 3) substituents independently selected from the group consisting of
halogen (including F, Cl, Br);
OH (hydroxyl);
C≡N (cyano);
$NO_2$ (nitro);
$C_1$-$C_6$ alky optionally comprising up to 5 halogen atoms (e.g. F), such as $CH_3$, $CF_3$, or $CHF_2$;
$C_1$-$C_3$ alkyl comprising up to 3 OH groups, such as $CH_2OH$;
$C_2$-$C_6$ alkenyl, such as —CH═$CH_2$;
$C_1$-$C_6$ alkoxy optionally comprising up to 3 halogen atoms (e.g. F), such as $OCH_3$, $OCH_3$, $OCF_3$;
$C_1$-$C_3$ alkoxy $C_1$-$C_3$ alkyl, such as 2-methoxy-ethyl;
$C_3$-$C_7$ cycloalkyl, such as cyclopropyl, cyclobutyl;
—C(O)$R^{1'}$ wherein $R^{10}$ is selected from $C_1$-$C_3$ alkyl;
—OC(O)$R^{11}$ wherein $R^{11}$ is selected from H, and $C_1$-$C_3$ alkyl;
—C(O)O—$R^{12}$ wherein $R^{12}$ is selected from hydrogen and $C_1$-$C_3$ alkyl;
—$(CH_2)_m$N($R^{13}$)$R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxo-thiomorpholine;
—$SR^{17}$ wherein $R^{17}$ is selected from hydrogen and $C_1$-$C_3$ alkyl; and
—$S(O)_2R^{18}$ wherein $R^{18}$ is selected from hydrogen and $C_1$-$C_3$ alkyl; with the proviso that when the aryl ring is substituted with two or more substituents, two substituents may form a cyclic ring together with the carbon atoms to which they are attached, and $C_5$-$C_{10}$ mono- or bicyclic heteroaryl wherein up to 2 C-atoms are replaced by a hetero atoms independently selected from sulfur, nitrogen, and oxygen, optionally substituted with up to four (e.g. 1, 2, or 3) substituents selected from the group consisting of halogen (including F, Cl, Br); OH (hydroxyl);

C≡N (cyano);

$NO_2$ (nitro);

$C_1$-$C_6$ alky optionally comprising up to 5 halogen atoms (e.g F), such as $CH_3$, $CF_3$, or $CHF_2$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—C(O)$R^{20}$ wherein $R^{20}$ is selected from $C_1$-$C_3$ alkyl;

—OC(O)$R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl);

—$(CH_2)_m$N($R^{23}$)$R^{24}$ wherein m is 0 or 1, $R^{23}$ is selected from hydrogen, $O_1$—$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxo-thiomorpholine;

—$SR^{27}$ wherein $R^{27}$ is selected from hydrogen and $C_1$-$C_3$ alkyl; and —$S(O)_2R^{28}$ wherein $R^{28}$ is selected from hydrogen and $C_1$-$C_3$ alkyl; and B represents a monovalent residue (b)

(b)

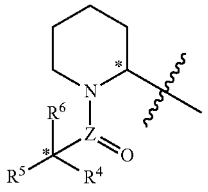

wherein $R^4$, $R^5$ and $R^6$ form together with the carbon atom to which they are attached a hydrocarbon group optionally comprising up to five (e.g. 1, 2, 3, 4) hetero atoms selected from O, N, S, and F (preferably the hydrocarbon group comprises 2 to 15 C-atoms (e.g. 3, 4, 5, 6, 7, 8, 9, 10, 11, 12, 13, or 14 C-atoms); and Z is either C, S or S(O).

In accordance with a second aspect there is provided a method of modulating (in-vitro and in-vivo modulation) of transient receptor potential melastatin member 8 (TRPM8) comprising bringing the receptor into contact with a compound of formula (I), or a salt or solvate thereof.

There is provided in a third aspect a method of inducing a cooling sensation in a human or animal comprising contacting the human or animal with a compound of formula (I), or a salt or solvate thereof.

There is provided in a fourth aspect consumer products, in particular consumer products which get into contact with the human skin and/or mucosa comprising a compound as defined by formula (I), or a salt or solvate thereof.

There is provided in a fifth aspect a composition comprising a cool sensation wherein the composition comprises at least one compound of formula (I), a salt or solvate thereof, and a further cooling compound.

There is provided in a sixth aspect pharmaceutical composition comprising one or more compounds as defined by formula (I), or a salt or solvate thereof.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION

The present invention is based, at least in part, on the surprising finding of a new class of chemical compounds which differ significantly in structural terms from the TRPM8 modulators known hitherto, that are capable to activate the TRPM8 ion channel, which brings about a $Ca^{2+}$ influx into the cold-sensitive neurons. The electrical signal produced as a result is ultimately perceived as sensation of coldness. Applicant surprisingly found that this class of chemical compounds as herein further described can provide long lasting cooling on the human skin and/or mucosa at very low concentrations.

Thus, there is provided in a first aspect a compound of formula (I), a salt or solvate thereof (in particular for use in providing cooling sensation)

(I)

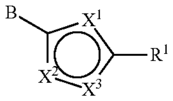

wherein one of $X^1$, $X^2$, and $X^3$ is >N—C(O)R and the other two are independently selected from C, N, and O, with the proviso that not both of them are C, and wherein R is selected from $C_1$-$C_{15}$ hydrocarbon residue optionally comprising one heteroatom selected from O and S;

and a) $R^1$ is H; and B represents a monovalent residue (a)

(a)

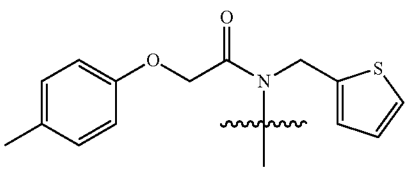

or b) $R^1$ is selected from halogen (including Br, $C_1$, and F), $C_6$-$C_{10}$ aryl (e.g. phenyl, or naphthyl) optionally substituted with up to four (e.g. 1, 2, or 3) substituents independently selected from the group consisting of halogen (including F, Cl, Br);

OH (hydroxyl);

C≡N (cyano);

$NO_2$ (nitro);

$C_1$-$C_6$ alky optionally comprising up to 5 halogen atoms (e.g. F), such as $CH_3$, $CF_3$, or $CHF_2$;

$C_1$-$C_3$ alkyl comprising up to 3 OH groups, such as $CH_2OH$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—C(O)$R^{10}$ wherein $R^{10}$ is selected from $C_1$-$C_3$ alkyl;

—OC(O)$R^{11}$ wherein $R^{11}$ is selected from H, and $C_1$-$C_3$ alkyl;

—C(O)O—$R^{12}$ wherein $R^{12}$ is selected from hydrogen and $C_1$-$C_3$ alkyl;

—$(CH_2)_m$N($R^{13}$)$R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxo-thiomorpholine;

—$SR^{17}$ wherein $R^{17}$ is selected from hydrogen and $C_1$-$C_3$ alkyl; and —S(O)$_2R^{18}$ wherein $R^{18}$ is selected from hydrogen and $C_1$-$C_3$ alkyl;

with the proviso that when the aryl ring is substituted with two or more substituents, two substituents may form a cyclic ring together with the carbon atoms to which they are attached, and $C_5$-$C_{10}$ mono- or bicyclic heteroaryl wherein up to 2 C-atoms are replaced by a hetero atoms independently selected from sulfur, nitrogen, and oxygen, optionally substituted with up to four (e.g. 1, 2, or 3) substituents selected from the group consisting of halogen (including F, Cl, Br); OH (hydroxyl);

C≡N (cyano);

$NO_2$ (nitro);

$C_1$-$C_6$ alky optionally comprising up to 5 halogen atoms (e.g. F), such as $CH_3$, $CF_3$, or $CHF_2$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—C(O)$R^{20}$ wherein $R^{20}$ is selected from $C_1$-$C_3$ alkyl;

—OC(O)$R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl);

—$(CH_2)_m$N($R^{23}$)$R^{24}$ wherein m is 0 or 1, $R^{23}$ is selected from hydrogen, $C_1$-$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxothiomorpholine;

—$SR^{27}$ wherein $R^{27}$ is selected from hydrogen and $C_1$-$C_3$ alkyl; and —S(O)$_2R^{28}$ wherein $R^{28}$ is selected from hydrogen and $C_1$-$C_3$ alkyl;

and

B represents a monovalent residue (b)

(b)

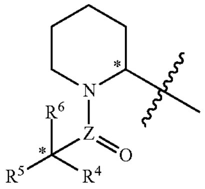

wherein $R^4$, $R^5$ and $R^6$ form together with the carbon atom to which they are attached a hydrocarbon group optionally comprising up to five (e.g. 1, 2, 3, 4) hetero atoms selected from O, N, S, and F (preferably the hydrocarbon group comprises 2 to 15 C-atoms (e.g. 3, 4, 5, 6, 7, 8, 9, 10, 11, 12, 13, or 14 C-atoms); and Z is either C, S or S(O).

Further non-limiting examples are compounds of formula (Ib), a salt or solvate thereof (Ib)

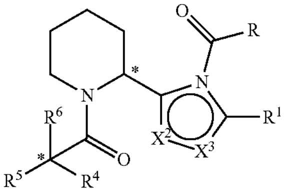

wherein

R is selected from $C_1$-$C_{15}$ hydrocarbon residue, optionally comprising one heteroatom selected from 0, and S;

$R^1$ is selected from halogen (including Br, $C_1$, and F), $C_6$-$C_{10}$ aryl (e.g. phenyl, or naphthyl) optionally substituted with up to four (e.g. 1, 2, or 3) substituents independently selected from the group consisting of halogen (including F, Cl, Br); OH (hydroxyl); C═N (cyano); $NO_2$ (nitro);

$C_1$-$C_6$ alky optionally comprising up to 5 halogen atoms (e.g F), such as $CH_3$, $CF_3$, or $CHF_2$;

$C_1$-$C_3$ alkyl comprising up to 3 OH groups, such as $CH_2OH$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—C(O)$R^{10}$ wherein $R^{10}$ is selected from $C_1$-$C_3$ alkyl;

—OC(O)$R^{11}$ wherein $R^{11}$ is selected from H, and $C_1$-$C_3$ alkyl;

—C(O)O—$R^{12}$ wherein $R^{12}$ is selected from hydrogen and $C_1$-$C_3$ alkyl;

$(CH_2)_m$N($R^{13}$)$R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxothiomorpholine;

—$SR^{17}$ wherein $R^{17}$ is selected from hydrogen and $C_1$-$C_3$ alkyl; and —$S(O)_2R^{18}$ wherein $R^{18}$ is selected from hydrogen and $C_1$-$C_3$ alkyl;

with the proviso that when the aryl ring is substituted with two or more substituents two substituents may form a cyclic ring together with the carbon atoms to which they are attached, and $C_5$-$C_{10}$ mono- or bicyclic heteroaryl wherein up to 2 C-atoms are replaced by a hetero atoms independently selected from sulfur, nitrogen, and oxygen, optionally substituted with up to four (e.g. 1, 2, or 3) substituents selected from the group consisting of halogen (including F, Cl, Br); OH (hydroxyl); C≡N (cyano); $NO_2$ (nitro);

$C_1$-$C_6$ alky optionally comprising up to 5 halogen atoms (e.g F), such as $CH_3$, $CF_3$, or $CHF_2$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—$C(O)R^{20}$ wherein $R^{20}$ is selected from $C_1$-$C_3$ alkyl;

—$OC(O)R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl);

—$(CH_2)_mN(R^{23})R^{24}$ wherein m is 0 or 1, $R^{23}$ is selected from hydrogen, $C_1$-$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxothiomorpholine;

—$SR^{27}$ wherein $R^{27}$ is selected from hydrogen and $C_1$-$C_3$ alkyl; and —$S(O)_2R^{28}$ wherein $R^{28}$ is selected from hydrogen and $C_1$-$C_3$ alkyl;

$R^4$, $R^5$ and $R^6$ form together with the carbon atom to which they are attached a hydrocarbon group optionally comprising up to five (e.g. 1, 2, 3, 4) hetero atoms selected from O, N, S, and F (preferably the hydrocarbon group comprises 2 to 15 C-atoms (e.g. 3, 4, 5, 6, 7, 8, 9, 10, 11, 12, 13, or 14 C-atoms);

and $X^2$ and $X^3$ are independently selected from C, N, and O, with the proviso that either $X^2$ or $X^3$ is not C.

Further non-limiting examples are compounds for formula (Ic), a salt or solvate thereof (Ic)

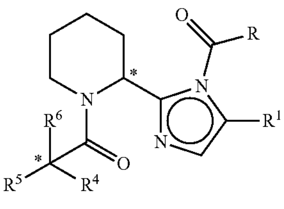

wherein R, $R^1$, and $R^4$ to $R^6$ have the same meaning as for formula (Ib).

Further non-limiting examples are compounds for formula (Id), a salt or solvate thereof (Id)

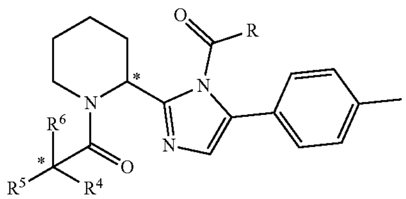

wherein R, and $R^4$ to $R^6$ have the same meaning as for formula (Ic).

Further non-limiting examples are compounds for formula (Ie), a salt or solvate thereof (Ie)

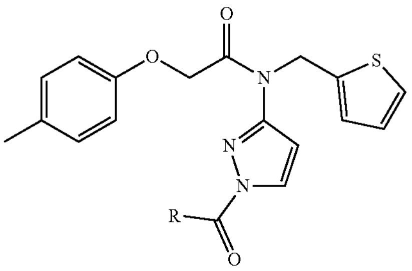

wherein R is selected from $C_1$-$C_{15}$ hydrocarbon residue, optionally comprising one heteroatom selected from O, and S.

Further non-limiting examples are compounds of formula (I), (Ia), (Ib), (Ic), (Id) and (Ie) wherein R is selected from the group consisting of $C_1$-$C_{15}$ linear or branched alkyl (including ethyl, iso-propyl, linear $C_4$-$C_{15}$ alkyl, such as $C_5$-, $C_6$-, $C_7$-, $C_8$-, $C_9$-, $C_{10}$-, $C_{11}$, $C_{12}$-, $C_{13}$-, and $C_{14}$-alkyl), phenyl, 2-isopropyl-5-methylcyclohexane-1-yl (including (1R, 2S, 5R)-2-isopropyl-5-methylcyclohexane-1-yl), 2-thia-but-3-yl, 2-oxa-prop-1-yl and 3-phenyl-2-oxa-prop-1-yl.

Further non-limiting examples are compounds of formula (I), (Ia), (Ib), (Ic) and (Id) wherein $R^4$ is selected from hydrogen and methyl;

$R^5$ is selected from hydrogen, $C_1$-$C_2$ alkyl, and $C_2$-$C_3$ alkenyl; and $R^6$ is selected from $C_1$-$C_4$ alkyl, $C_2$-$C_5$ alkenyl containing one or two double bonds, $C_1$-$C_3$ alkoxy, $C_1$-$C_4$ alkyl-C(O)—, $C_1$-$C_4$ alkyl-S—, $C_1$-$C_4$ alkyl-$SCH_2$—, $C_1$-$C_4$ alkenyl-S—, $C_1$-$C_4$ alkyl-S(O)—, $C_1$-$C_4$ alkyl-$S(O)_2$—, $C_1$-$C_4$ alkenyl-S(O)—, $C_1$-$C_4$ alkenyl-$S(O)_2$—, —SH, $CF_3S$—, cyclopropyl, cyclobutyl, furyl (e.g. 2-furyl or 3-furyl) optionally substituted with methyl, $C_1$-$C_6$ fluoro-alkyl (such as pentafuloroethyl, difluoromethyl, trifluoromethyl, 2,2,2-trifluoroethyl or difluoroethyl), and —$NR^{30}R^{31}$ wherein $R^{30}$ and $R^{31}$ are independently selected from hydrogen and $C_1$-$C_3$ alkyl;

or $R^6$ and $R^5$ form together with the carbon atom to which they are attached a) a carbonyl group (C═O) or vinyl group (C═$CR^{32}R^{33}$ wherein $R^{32}$ and $R^{33}$ are independently selected from H or $C_1$-$C_3$ alkyl); or b) a 3 to 7-membered saturated or unsaturated cycle ring comprising up to 3 heteroatoms selected from oxygen, nitrogen and sulfur, wherein the cyclic ring is optionally substituted with one or two groups independently selected from $C_1$-$C_3$ alkyl (e.g. methyl, ethyl, isopropyl), $C_1$-$C_3$ alkoxy; (e.g. $R^5$ and $R^6$ form together with the carbon atom to which they are attached thiodiazole, or furanyl).

Further non-limiting examples are compounds of formula (I), (la), (Ib), (Ic) and (Id) wherein $R^4$ is selected from hydrogen and methyl; $R^5$ is selected from hydrogen, $C_1$-$C_2$ alkyl, $C_2$-$C_3$ alkenyl; and $R^6$ is selected from $C_1$-$C_4$ alkyl, $C_2$-$C_5$ alkenyl containing one or two double bonds, $C_1$-$C_3$ alkoxy, $C_1$-$C_4$ alkyl-C(O)—, $C_1$-$C_4$ alkyl-S—, $C_1$-$C_4$ alkyl-$SCH_2$—, $C_1$-$C_4$ alkenyl-S—, $C_1$-$C_4$ alkyl-S(O)—, $C_1$-$C_4$ alkyl-$S(O)_2$—, $C_1$-$C_4$ alkenyl-S(O)—, $C_1$-$C_4$ alkenyl-$S(O)_2$—, —SH, $CF_3S$—, cyclopropyl, cyclobutyl, furyl (e.g. 2-furyl or 3-furyl) optionally substituted with methyl, $C_1$-$C_6$ fluoro-alkyl (such as pentafuloroethyl, difluoromethyl, trifluoromethyl, 2,2,2-trifluoroethyl or difluoroethyl), and —$NR^{30}R^{31}$ wherein $R^{30}$ and $R^{31}$ are independently selected from hydrogen and $C_1$-$C_3$ alkyl.

Further non-limiting examples are compounds of formula (I), (Ia), (Ib), (Ic) and (Id) wherein $R^4$, $R^5$ and $R^6$ form together with the carbon atom to which they are attached a hydrocarbon group selected from 3-thiabut-2-yl, 2-methyl-3-thiabut-2-yl, 3-thiapent-2-yl, 4-thiapent-2-yl, 2-thiaprop-1-yl, 2-methyl-3-thiapent-2-yl, 3-oxo-3-thiabut-2-yl, 3-oxo-2-methyl-3-thiabut-2-yl, 3-oxo-3-thiapent-2-yl, 4-oxo-4-thiapent-2-yl, 2-oxo-2-thiaprop-1-yl, 3-oxo-2-methyl-3-thiapent-2-yl, but-2-yl, pent-2-yl, but-3-en-2-yl, pent-3-en-2-yl, but-2-en-2-yl, pent-2-en-2-yl, but-1-en-2-yl, pent-1-en-2-yl, 2-methylbut-2-yl, 2-methylpent-2-yl, 2-methylbut-3-en-2-yl, 3-methylbut-2-yl, 3-methylbut-3-en-2-yl, 3-methylbut-2-en-2-yl, 2,3-dimethylbut-2-yl, 2,3-dimethylpent-2-yl, 2,3-dimethylbut-3-en-2-yl, 2,3-dimethylpent-3-en-2-yl, 2-methylpent-3-en-2-yl, prop-2-yl, prop-1-yl, ethyl, cyclopropyl, 1,1-dimethylcycloprop-2-yl, 1-methylcycloprop-2-yl, 1-methylcycloprop-1-yl, 3-thiahex-5-en-2-yl, 2-methyl-3-thiahex-5-en-2-yl, 1-mercaptoeth-1-yl, 2-mercaptoprop-2-yl, 3,3,3-trifluoroprop-2-yl, 2-methyl-3,3,3-trifluoroprop-2-yl, 1-(2-furyl)eth-1-yl, 1-(5-methylfur-2-yl)eth-1-yl, 2-(2-furyl)prop-2-yl, 1-(3-furyl)eth-1-yl, 1-(5-methylfur-3-yl)eth-1-yl, 2-(3-furyl)prop-2-yl, 1-(2-tetrahydrofuryl)eth-1-yl, 2-(2-tetrahydrofuryl)prop-2-yl, 1-(3-tetrahydrofuryl)eth-1-yl, 2-(3-tetrahydrofuryl)prop-2-yl, 1-cyclopropyleth-1-yl, 2-cyclopropylprop-2-yl, 1-cyclobutyleth-1-yl, 2-cyclobutylprop-2-yl, cyclobutyl, cyclopentyl, pent-2-en-3-yl, 1-methoxyprop-1-yl, 1-methoxyeth-1-yl, 1,1,1-trifluorobut-3-yl and 3-thiacyclobut-1-yl.

Further non-limiting examples are compounds of formula (I), (Ia), (Ib), (Ic) and (Id) wherein $R^4$ is selected from hydrogen and methyl, $R^5$ is selected from hydrogen, $C_1$-$C_2$ alkyl, $C_2$-$C_3$ alkenyl, and $R^6$ is selected from $C_1$-$C_4$ alkyl, $C_2$-$C_5$ alkenyl containing one or two double bonds, $C_1$-$C_3$ alkoxy, $C_1$-$C_4$ alkyl-C(O)—, $C_1$-$C_4$ alkyl-S—, $C_1$-$C_4$ alkyl-$SCH_2$—, $C_1$-$C_4$ alkenyl-S—, $C_1$-$C_4$ alkyl-S(O)—, $C_1$-$C_4$ alkyl-$S(O)_2$—, $C_1$-$C_4$ alkenyl-S(O)—, $C_1$-$C_4$ alkenyl-$S(O)_2$—, and —SH.

Further non-limiting examples are compounds of formula (Ic) wherein $R^1$ is p-tolyl, and $R^4$, $R^5$ and $R^6$ form together with the carbon atom to which they are attached 2-methyl-3-thiabut-2-yl or but-2-yl.

Further non-limiting examples are compounds for formula (I), selected from the group consisting of 1-(2-(1-propionyl-4-(p-tolyl)-1 H-imidazol-2-yl)piperidin-1-yl)propan-1-one; 1-(2-(1-isobutyryl-4-(p-tolyl)-1H-imidazol-2-yl)piperidin-1-yl)-2-methylpropan-1-one; 2-(methylthio)-1-(2-(1-(2-(methylthio)propanoyl)-4-(p-tolyl)-1 H-imidazol-2-yl)piperidin-1-yl)propan-1-one; 1-(2-(1-acetyl-4-(p-tolyl)-1H-imidazol-2-yl)piperidin-1-yl)-2-(methylthio)propan-1-one; 1-(2-(1-isobutyryl-4-(p-tolyl)-1 H-imidazol-2-yl)piperidin-1-yl)-2-(methylthio)propan-1-one; 1-(2-(1-benzoyl-4-(p-tolyl)-1H-imidazol-2-yl)piperidin-1-yl)-2-(methylthio)propan-1-one; 1-(2-(1-((1R,2S,5R)-2-isopropyl-5-methylcyclohexane-1-carbonyl)-4-(p-tolyl)-1H-imidazol-2-yl)piperidin-1-yl)-2-(methylthio)propan-1-one; 1-(2-(1-acetyl-4-(p-tolyl)-1H-imidazol-2-yl)piperidin-1-yl)-2-methylbutan-1-one; 1-(2-(1-isobutyryl-4-(p-tolyl)-1H-imidazol-2-yl)piperidin-1-yl)-2-methylbutan-1-one; 1-(2-(1-((1R,2S,5R)-2-isopropyl-5-methylcyclohexane-1-carbonyl)-4-(p-tolyl)-1 H-imidazol-2-yl)piperidin-1-yl)-2-methylbutan-1-one; 1-(2-(1-(2-methoxyacetyl)-4-(p-tolyl)-1H-imidazol-2-yl)piperidin-1-yl)-2-methylbutan-1-one; 1-(2-(1-(2-(benzyloxy)acetyl)-4-(p-tolyl)-1H-imidazol-2-yl)piperidin-1-yl)-2-methylbutan-1-one; 1-(2-(1-(2-(methylthio)propanoyl)piperidin-2-yl)-4-(p-tolyl)-1H-imidazol-1-yl)dodecan-1-one; 1-(2-(1-(2-methylbutanoyl)piperidin-2-yl)-4-(p-tolyl)-1 H-imidazol-1-yl)dodecan-1-one; 1-(2-(1-(2-(methylthio)propanoyl)piperidin-2-yl)-4-(p-tolyl)-1H-imidazol-1-yl)hexan-1-one; 1-(2-(1-(2-methylbutanoyl)piperidin-2-yl)-4-(p-tolyl)-1 H-imidazol-1-yl)hexan-1-one; N-(1-benzoyl-1 H-pyrazol-3-yl)-N-(thiophen-2-ylmethyl)-2-(p-tolyloxy)acetamide; N-(1-isobutyryl-1H-pyrazol-3-yl)-N-(thiophen-2-ylmethyl)-2-(p-tolyloxy)acetamide; and N-(1-acetyl-1H-pyrazol-3-yl)-N-(thiophen-2-ylmethyl)-2-(p-tolyloxy)acetamide.

The compounds as defined by formula (I) (which encompass the compounds of formula (Ia), (Ib), (Ic), (Id), and (Ie)) comprise several chiral centers (two of which are indicated by * in the respective formulae) and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis. The compounds as defined by formula (I) (which encompass the compounds of formula (Ia), (Ib), (Ic), (Id) and (Ie)) may also exist in various tautomeric forms, including the 1 H-Imidazole—3H-Imidazole form. Accordingly, the chemical structures depicted herein encompass all possible sterioisomers and tautomeric forms of the illustrated compounds.

It is also noted that the compounds as defined by formula (I) (which encompass the compounds of formula (Ia), (Ib), (Ic), (Id) and (Ie)) may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are intended to be within the scope of the present invention.

"Solvate" means a compound formed by solvation (the combination of solvent molecules with molecules or ions of the solute), or an aggregate that consists of a solute ion or molecule, i.e., a compound as defined by formula (I) (which encompass the compounds of formula (Ia), (Ib) and (Ic)), with one or more solvent molecules. When water is the solvent, the corresponding solvate is "hydrate". Further suitable solvents can be but are not limited to: acetone, acetonitrile, benzene, cyclohexane, dihydrolevoglucosenone, methyl-tetrahydrofuran, pentylene glycol, ethylene glycol, petroleum ether, ethyl lactate, methyl lactate, propyl lactate, diethylether, tert-butyl methyl ether, dimethylsulfoxide, N,N-dimethylformamide, N,N-dimethylacetamide, dioxane, ethanol, ethyl acetate, ethylene glycol, diethylene glycol, propylene glycol, heptane, hexane, methanol, toluene and xylene.

"Salt" refers to a salt of a compound as defined by formula (I) (which encompass the compounds of formula (Ia), (Ib), (Ic), (Id) and (Ie)), which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as amino acids, acetic acid, trifluoroacetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The compounds as defined by formula (I) (which encompass the compounds of formula (Ia), (Ib), (Ic), (Id) and (Ie)) are "TRPM8 agonist", which means that they have an agonistic effect on the cellular $Ca^{2+}$ ion permeability of the TRPM8 channels.

Accordingly, by "TRPM8 agonist" is meant any compound, which when brought into contact with the TRPM8 receptor, produces an increase in fluorescence over background, using the FLIPR method as described, e.g., by Klein et al., (Chem. Senses 36: 649-658, 2011), which is also described in more details in the experimental part.

Accordingly there is provided in a second aspect a method of modulating (in-vitro and in-vivo modulation) of transient receptor potential melastatin member 8 (TRPM8) comprising bringing the receptor into contact with a compound of formula (I), or a salt or solvate thereof.

In certain embodiments of the second aspect of the invention the modulating method is an in-vitro method.

There is provided in a third aspect a non-medical method of inducing a cooling sensation in a human or animal comprising contacting the human or animal with a compound of formula (I) (which encompass the compounds of formula (Ia), (Ib), (Ic), (Id) and (Ie)), or a salt or solvate thereof.

In certain embodiments, the method is a method of achieving a cooling effect on the skin or mucosa comprising contacting the skin or mucosa with a product comprising one or more compounds of formula (I), or a salt or solvate thereof.

Without wishing to be bound by theory it is believed that the acyl group (>N—C(O)R) of the compound of formula (I) as herein defined may get cleaved under certain conditions, thus slowly releasing a compound of formula (I')

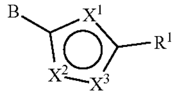

(I')

wherein one of $X^1$, $X^2$, and $X^3$ is >NH and the other two are independently selected from C, N, and O, with the proviso that not both of them are C; and $R^1$ and B have the same meaning as for formula (I).

The nature of the acyl group may allow the modulation of the release kinetics of the compound of formula (I'). Compounds of formula (I') (i.e. the hydrolysed compounds of formula (I)) are, for example, disclosed in the patent application PCT/EP2020/079009 (WO 2021/074281).

Thus there is provided in a further embodiment, a method of achieving a cooling effect on the skin or mucosa comprising hydrolysing the acetyl group (>N—C(O)R) of the compound of formula (I) before getting in contact with the skin or mucose.

The compounds of formula (I) (which encompass the compounds of formula (Ia), (Ib), (Ic), (Id) and (Ie)), may be applied directly or as a solution or suspension, comprising an effective amount of a compound of formula (I). An amount to be effective depends, inter alia, upon the target TRPM8 area of the body but also on the cooling potency of compound or mixture of compounds.

There is provided in a fourth aspect consumer products, in particular consumer products which get into contact with the human skin and/or mucosa comprising a compound as defined by formula (I), which encompass the compounds of formula (Ia), (Ib), (Ic), (Id) and (Ie).

Consumer products which get in contact with the mucosa include, but are not limited to food products, beverages, chewing gum, tobacco and tobacco replacement products, dental care products, personal care products, including lip care products, sexual health and intimate care products.

In certain embodiments dental care products are oral care products, tooth care products, cleaners for dental prostheses, adhesives for dental prostheses, and the like.

In certain embodiments food products are iced consumable products such as ice cream, sorbet; confectioneries such as candies and chocolates; food products containing mint or mint flavour, sauces, dairy products such as milk-based drinks and yoghurts; and snacks.

In certain embodiments tobacco replacement products are liquids or solids which are suitable to be consumed by electrical means, e.g., liquids to vape.

In certain embodiments personal care products getting in contact with the mucosa are lip balms, nose sprays and eye drops.

Consumer products which get in contact with the human skin include, but are not limited to cosmetic products. In certain embodiments cosmetic products are skincare products, especially bath products, skin washing and cleansing products, skincare products, eye makeup, nail care products, foot care products, and the like. In certain embodiments cosmetic products are products with specific effects, especially sunscreens, insect repellent products, tanning products, de-pigmenting products, deodorants, antiperspirants, hair removers, and shaving products. In a certain embodiments cosmetic products are hair care products, especially hair shampoos, hair care products, hair setting products, hair-shaping products, and hair coloring products as well as scalp-care products such as scalp-cooling shampoos and creams.

In certain embodiments, the consumer product is selected from air care products, such as an air freshener or a "ready to use" powdered air freshener which can be used in the home space (rooms, refrigerators, cupboards, shoes or car) and/or in a public space (halls, hotels, malls, etc..).

The consumer products can be in any physical form, such as a solid, semi-solid, plaster, solution, suspension, lotion, cream, foam, gel, paste, or a combination thereof. The physical form of the consumer product suitable manly depends on the specific actions, such as cleaning, softening, caring, cooling, and the like, such a consumer product should fulfill.

In a certain embodiment consumer products getting in contact with the human skin are fabric care products (such as fabric detergents, fabric conditioner (including tumble dryer sheets), and scent boosters (liquid or solid)) which in a first step are applied to a fabric, e.g., when washing the fabric, said treaded fabrics then getting in contact with the human skin.

The level of use for compounds of the present invention (compounds as defined by formula (I), which encompass compounds of formula (Ia), (Ib), (Ic), (Id) and (Ie)) depend, inter alia, upon the target TRPM8 area of the body but also on the cooling potency of compound or mixture of compounds. For examples in an oral application of a compound of the present invention, such as dentifrice, floss, chewing gum, or white strip, the levels of use may be from about 0.00001% (0.01 ppm) to about 0.1% (1000 ppm); from about 0.00005% (0.5 ppm) to about 0.1% (1000 ppm); from about 0.0001% (1 ppm) to about 0.05% (500 ppm); or from about 0.001% (10 ppm) to about 0.01% (100 ppm) by weight of the composition. When a compound of the present invention is used in a mouthwash, the level of use may be from about 0.000001% (10 ppb) to about 0.01% (100 ppm) or from about 0.0001% (1 ppm) to about 0.001% (10 ppm) by weight of the composition. When a compound of the present invention is delivered topically, for example in shampoos and lotions the levels may be from about 0.001% (10 ppm) to about 0.5% (5000 ppm) by weight of the composition or from about 0.01% (100 ppm) to about 0.4% (4000 ppm) by weight of the composition.

The cooling potency (strength) of a compound is defined by its $EC_{50}$ value. $EC_{50}$(half maximal effective concentration) refers to the concentration of a compound which induces a response halfway between the baseline and maximum after a specified exposure time. It is commonly used as a measure of potency. $EC_{50}$ is a measure of concentration, expressed in μM (μmolar) unites, where 1 μM is equivalent to 1 μmol/L.

Compounds with an $EC_{50}$ of 10 μM or less are perceived by the human as cooling. The lower the $EC_{50}$ value the higher the cooling potency. For example, compounds having an $EC_{50}$ value of about 0.1 μM are perceived as strong cooling compounds.

Cooling properties of a compound however are not only defined by its strength (potency; $EC_{50}$) but also its longevity, which refers to the period of time (in minutes) over which a cooling effect is perceived. The longevity can range from a few seconds after rinsing to several hours or even days. In the context of oral care products, a preferred "long-lasting" effect ranges typically between 20 minutes after rinsing to 3 hours.

The compounds as defined by formula (I) (which encompass the compounds of formula (Ia), (Ib), (Ic), (Id) and (Ie)) are generally well soluble in water at the desired concentrations. However, to increase the solubility, a specific isomer may be used instead of an isomeric mixture. As is well known to the person skilled in the art, cis/trans-Isomers and/or diastereomers may have different solubility properties and thus either a mixture of isomers or the individual isomers may be selected for the use in consumer products, depending on which cooling effect is to be achieved.

The compounds of formula (I) (which encompass the compounds of formula (Ia), (Ib), (Ic), (Id) and (Ie)) are very potent at relative low concentrations. Thus it is preferred to prepare a stock solution which is further diluted, before admixing it to a consumer product. Beside water, particular suitable solvents are triacetin and propylene glycol. One may also mention acetone, benzyl alcohol, dihydrolevoglucosenone, methyl-tetrahydrofuran, pentylene glycol, ethylene glycol, ethyl lactate, methyl lactate, propyl lactate, dimethylsulfoxide, ethanol, ethyl acetate, ethylene glycol, diethylene glycol, propylene glycol, and triacetin which are suitable solvents for the compounds of formula (I) (which encompass the compounds of formula (Ia), (Ib), (Ic), (Id) and (Ie)). But other solvent systems comprising surfactants may also be used.

To modify the cooling effect of a compound as defined herein by formula (I) (which encompass the compounds of formula (Ia), (Ib), (Ic), (Id) and (Ie)), the compound, a salt or solvate thereof may be combined with a compound selected from calcium ions and salts, magnesium ions and salts, arginine, or any chelating agent which is able to bind calcium or magnesium.

These compounds are known to be able to modulate the concentration of such ions in the extracellular space and therefore influence the response of the TRPM8 ion-channel, leading to a change in the perceived cooling effect.

According to Kizilbash et al. (WO2019/121193 A1) both, the cooling intensity and the flavour intensity may be enhanced when combined with agents which possess the property to potentiating said effects. Thus the compounds as defined herein by formula (I) may be combined in one particular embodiment with potentiating agents disclosed in WO2019/121193 which is incorporated by reference, in particular with regard to the potentiating agents.

As a further enhancement agent one may cite N-lactoyl ethanolamine (2-hydroxy-N-(2-hydroxyethyl)propanamide; CAS 5422-34-4) which is known as an enhancer for cooling agents, for example, from PCT International publication WO 2008/107137 which is incorporated by reference, in particular with regard to the cooling enhancing substances as defined by formula (I).

The compounds of formula (I) (which encompass the compounds of formula (Ia), (Ib), (Ic), (Id) and (Ie)), might be used in combination with other cooling compounds known in the art.

Thus there is provided in a fifth aspect a composition comprising a cool sensation wherein the composition comprises at least one compound of formula (I), a salt or solvate thereof, and a further cooling compound.

In one particular embodiment the compounds of formula (I) (which encompass the compounds of formula (Ia), (Ib), (Ic), (Id) and (Ie)) may be combined with menthol (e.g., in form of peppermint oil, and/or spearmint oil), menthone, p-menthanecarboxamides, N-2,3-trimethyl-2-isopropyl-butanamide (WS-23), menthyl lactate (Frescolat® ML), menthone glycerol acetal (Frescolat® MGA), 3-(1-menthoxy)-propane-1,2-diol (TK-10), p-menthane-3,8-diol (known as Coolact 38D), isopulegol (known as Coolact P), monomenthyl succinate (Physcool®), monomenthyl glutarate, o-menthylglycerol, menthyl N,N-dimethylsuccinamate, 2-(sec-butyl)cyclohexan-1-one (Freskomenthe), N-(pyrazol-3-yl)-N-(thiophen-2-ylmethyl)-2-(p-tolyloxy)acetamide, 2-(4- ethylphenoxy)-N-(pyrazol-3-yl)-N-(thiophen-2-ylmethyl) acetamide, 3-(benzo[d][1,3]dioxol-5-yl)-N,N-diphenylacrylamide, 4-(2-(4-allyl-2,6-dimethoxyphenoxy)-1-ethoxypropyl)-2-methoxyphenol, 4-(2-(4-allyl-2,6-dimethoxyphenoxy)-1-((2-isopropyl-5-methylcyclohexyl) oxy)propyl)-2-methoxyphenol (including 4-(2-(4-allyl-2,6-dimethoxyphenoxy)-1-(((1S,2R,5S)-2-isopropyl-5-methylcyclohexyl)oxy)propyl)-2-methoxyphenol) and 4-(2-(4-allyl-2,6-dimethoxyphenoxy)-1-(((1R,2S,5R)-2-isopropyl-5-methylcyclohexyl)oxy)propyl)-2-methoxy-phenol), N-(2-Hydroxy-2-phenylethyl)-2-isopropyl-5,5-dimethylcyclohexane-1-carboxamide, N-(4-(Cyanomethyl) phenyl)-2-isopropyl-5,5-dimethylcyclohexanecarboxamide, and N-(3-Hydroxy-4-methoxyphenyl)-2-isopropyl-5,5-dimethylcyclohexanecarboxamide.

Examples of p-methanecarboxamides include compounds such as N-ethyl-p-menthan-3-carboxamide (known commercially as WS-3), N-ethoxycarbonylmethyl-p-menthan-3-carboxamide (WS-5), N-(4-methoxyphenyl)-p-menthan-3-carboxamide (WS-12) and N-tert-butyl-p-menthan-3-carboxamide (WS-14), N-(4-(cyanomethyl)phenyl)-2-isopropyl-5-methylcyclohexane-1-carboxamide (known commercially as Evercool 180), 2-isopropyl-5-methyl-N-(2-(pyridin-2-yl)ethyl)cyclohexane-1-carboxamide (known commercially as Evercool 190), and (1R,2S,5R)—N—((S)-2-((R)-2-aminopropanamido)-2-phenylethyl)-2-isopropyl-5-methylcyclohexane-1-carboxamide.

In order to achieve more than just a cooling effect, the compounds of formula (I) (which encompass the compounds of formula (Ia), (Ib), (Ic), (Id) and (Ie)), a salt or solvate thereof, may be combined with other actives, such as, flavours, fragrances, and sweetening agents.

Examples of flavour ingredients include natural flavors, artificial flavors, spices, seasonings, and the like. Exemplary flavor ingredients include synthetic flavor oils and flavoring aromatics and/or oils, oleoresins, essences, and distillates, and a combination comprising at least one of the foregoing.

Flavor oils include spearmint oil, cinnamon oil, oil of wintergreen (methyl salicylate), peppermint oil, Japanese mint oil, clove oil, bay oil, anise oil, *eucalyptus* oil, thyme oil, cedar leaf oil, oil of nutmeg, allspice, oil of sage, mace, oil of bitter almonds, and *cassia* oil; useful flavoring agents include artificial, natural and synthetic fruit flavors such as vanilla, and citrus oils including lemon, orange, lime, grapefruit, yuzu, sudachi, and fruit essences including apple, pear, peach, grape, raspberry, blackberry, gooseberry, blueberry, strawberry, cherry, plum, prune, raisin, cola, guarana, neroli, pineapple, apricot, banana, melon, apricot, cherry, tropical fruit, mango, mangosteen, pomegranate, *papaya*, and so forth.

Additional exemplary flavors imparted by a flavoring composition include a milk flavor, a butter flavor, a cheese flavor, a cream flavor, and a yogurt flavor; a vanilla flavor; tea or coffee flavors, such as a green tea flavor, an oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an *angelica* flavor, a fennel flavor, an allspice flavor, a cinnamon flavor, a chamomile flavor, a mustard flavor, a cardamom flavor, a caraway flavor, a cumin flavor, a clove flavor, a pepper flavor, a coriander flavor, a *sassafras* flavor, a savory flavor, a Zanthoxyli Fructus flavor, a *perilla* flavor, a juniper berry flavor, a ginger flavor, a star anise flavor, a horseradish flavor, a thyme flavor, a tarragon flavor, a dill flavor, a *capsicum* flavor, a nutmeg flavor, a basil flavor, a marjoram flavor, a rosemary flavor, a bayleaf flavor, and a wasabi (Japanese horseradish) flavor; a nut flavor such as an almond flavor, a hazelnut flavor, a macadamia nut flavor, a peanut flavor, a pecan flavor, a pistachio flavor, and a walnut flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor.

Generally any flavoring or food additive (including food colors) such as those described in "Essential guide to food additives", Third edition 2008, page 101-321 (ISBN: 978-1-905224-53-0) by Leatherhead Food International Ltd., can be used. The publication is incorporated herein by reference.

In one particular embodiment the compounds of formula (I) (which encompass the compounds of formula (Ia), (Ib), (Ic), (Id) and (Ie)) may be combined with anethole, menthol laevo, carvone laevo, ethyl maltol, vanillin, eucalyptol, eugenol, menthol racemic, cis-3-hexenol, linalol, mint oil (e.g. peppermint *arvensis* oil, peppermint *piperita* oil, spearmint native oil, spearmint scotch oil), corylone, ethyl butyrate, cis-3-hexenyl acetate, citral, *eucalyptus* oil, ethylvanillin, methyl salicylate, 2'-hydroxypropiophenone, ethyl acetate, methyl dihydro jasmonate, geraniol, lemon oil, iso amyl acetate, thymol, ionone beta, linalyl acetate, decanal, (±)-dihydromint lactone (3,6-dimethyl-3a,4,5,6,7,7a-hexahydro-3H-benzofuran-2-one), cis jasmone, ethyl hexanoate, melonal (2,6-dimethylhept-5-enal), citronellol, ethyl aceto acetate, nutmeg oil and clove oil, or mixtures thereof.

In one specific embodiment the compound of formula (I) is a compound of formula (Ic) wherein $R^1$ is p-tolyl, and $R^4$, $R^5$ and $R^6$ form together with the carbon atom to which they are attached 2-methyl-3-thiabut-2-yl or but-2-yl.

Examples of sweetening agents include, but are not limited to, sucrose, fructose, glucose, high fructose corn syrup, corn syrup, xylose, arabinose, rhamnose, erythritol, xylitol, mannitol, sorbitol, inositol, acesulfame potassium, aspartame, neotame, sucralose, and saccharine, and mixtures thereof; trilobatin, hesperetin dihydrochalcone glucoside, naringin dihydrochalcone, mogroside V, Luo Han Guo extract, rubusoside, *rubus* extract, glycyphyllin, isomogroside V, mogroside IV, siamenoside I, neomogroside, mukurozioside llb, (+)-hernandulcin, 4β-hydroxyhernandulcin, baiyunoside, phlomisoside I, bryodulcoside, bryoside bryonoside, abrusosides A-E, cyclocarioside A, cyclocaryoside I, albiziasaponins A-E, glycyrrhizin, araboglycyrrhizin, periandrins I-V, pterocaryosides A and B, osladin, polypodosides A and B, telosmoside A8-18, phyllodulcin, huangqioside E neoastilbin, monatin, 3-acetoxy-5,7-dihydroxy-4'-methoxyflavanone, 2R,3R—(+)-3-Acetoxy-5,7,4'-trihydroxyflavanone, (2R,3R)-dihydroquercetin 3-O-acetate, dihydroquercetin 3-O-acetate 4'-methyl ether, brazzein, curculin, mabinlin, monellin, neoculin, pentadin, thaumatin, and combinations thereof. Some of the compounds listed above are known sweetness enhancers as well as sweeteners. When used as sweetness enhancers they are normally used below their sweetness detection thresholds.

In certain embodiments, the compounds of formula (I) may be combined with additional ingredients collectively refereed to orally acceptable carrier materials.

In some aspects, the orally acceptable carrier may comprise one or more compatible solid or liquid excipients or diluents which are suitable for topical oral administration. By "compatible," as used herein, is meant that the components of the composition are capable of being commingled without interaction in a manner which would substantially reduce stability and/or efficacy. The carriers can include the usual and conventional components of dentifrices, non-abrasive gels, subgingival gels, mouthwashes or rinses, mouth sprays, chewing gums, lozenges and breath mints. The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433, to Benedict. Carrier materials for biphasic dentifrice formulations are disclosed in U.S. Pat. Nos. 5,213,790; 5,145,666 and 5,281,410 all to Lukacovic et al., and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955, to Grabenstetter et al.. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani. Carriers suitable for the preparation of compositions of the present disclosure are well known in the art. Their selection will depend on secondary considerations like taste, cost, and shelf stability, and the like.

Further suitable types of orally acceptable carrier materials or excipients are listed in WO2010/059289, in particular on page 17-31, which is incorporated by reference. Scientific literature points out that the activation of TRPM8 channels may be useful for the treatment of most TRPM8-mediated pathologies (J. Med. Chem. 2016, 59 (22), 10006-10029). Thus one may assume that the compounds of formula (I) might also be suitable for treating prostate carcinomas, bladder weakness, inflammation, or pain comprising contacting a patient with one or more compounds of formula (I) as defined herein. One may also assume that the compounds of formula (I) as defined herein are suitable for alleviating the symptoms of coughs and colds, irritations, sore throat or hoarseness, as well as the treatment of laryngopharyngeal dysphagia (Int. J. Mol. Sci. 2018, 19, 4113).

Thus there is provided in a sixth aspect pharmaceutical composition comprising one or more compounds as defined by formula (I) (which encompass compounds of formula (Ia), (Ib), (Ic), (Id) and (Ie)), or a salt or solvate thereof.

Depending upon the particular treatment regimen contemplated, pharmaceutical compositions comprising one or more compounds of formula (I) may be administered parenterally, topically, orally, or locally. The pharmaceutical compositions may be a liquid, suspensions or a solid formulation.

In certain embodiments, the pharmaceutical composition is nasal spray, topical cream, skin sprays, throat spray, eye drops, or cough syrup.

The compounds of formula (I) as hereinabove defined are not described in the literature and are thus novel in their own right.

Thus, there is provided in a further aspect of the invention a compound of formula (I)

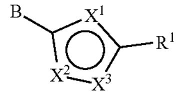

(I)

wherein one of $X^1$, $X^2$, and $X^3$ is >N—C(O)R and the other two are independently selected from C, N, and O, with the proviso that not both of them are C, and wherein R is selected from $C_1$-$C_{15}$ hydrocarbon residue optionally comprising one heteroatom selected from O and S;

and c) $R^1$ is H; and B represents a monovalent residue (a)

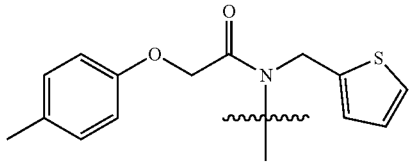

(a)

or d) $R^1$ is selected from halogen (including Br, $C_1$, and F), $C_6$-$C_{10}$ aryl (e.g. phenyl, or naphthyl) optionally substituted with up to four (e.g. 1, 2, or 3) substituents independently selected from the group consisting of
 halogen (including F, Cl, Br);
 OH (hydroxyl);
 C≡N (cyano);
 $NO_2$ (nitro);
 $C_1$-$C_6$ alky optionally comprising up to 5 halogen atoms (e.g F), such as $CH_3$, $CF_3$, or $CHF_2$;
 $C_1$-$C_3$ alkyl comprising up to 3 OH groups, such as $CH_2OH$;
 $C_2$-$C_6$ alkenyl, such as —CH═$CH_2$;
 $C_1$-$C_6$ alkoxy optionally comprising up to 3 halogen atoms (e.g. F), such as $OCH_3$, $OCH_3$, $OCF_3$;
 $C_1$-$C_3$ alkoxy $C_1$-$C_3$ alkyl, such as 2-methoxy-ethyl;
 $C_3$-$C_7$ cycloalkyl, such as cyclopropyl, cyclobutyl;
 —C(O)$R^{1'}$ wherein $R^{10}$ is selected from $C_1$-$C_3$ alkyl;
 —OC(O)$R^{11}$ wherein $R^{11}$ is selected from H, and $C_1$-$C_3$ alkyl;
 —C(O)O—$R^{12}$ wherein $R^{12}$ is selected from hydrogen and $C_1$-$C_3$ alkyl;
 —$(CH_2)_m$N($R^{13}$)$R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxo-thiomorpholine;
 —$SR^{17}$ wherein $R^{17}$ is selected from hydrogen and $C_1$-$C_3$ alkyl; and
 —S(O)$_2R^{18}$ wherein $R^{18}$ is selected from hydrogen and $C_1$-$C_3$ alkyl;
 with the proviso that when the aryl ring is substituted with two or more substituents, two substituents may form a cyclic ring together with the carbon atoms to which they are attached, and $C_5$-$C_1$ mono- or bicyclic heteroaryl wherein up to 2 C-atoms are replaced by a hetero atoms independently selected from sulfur, nitrogen, and oxygen, optionally substituted with up to four (e.g. 1, 2, or 3) substituents selected from the group consisting of halogen (including F, Cl, Br); OH (hydroxyl);

C≡N (cyano);

$NO_2$ (nitro);

$C_1$-$C_6$ alky optionally comprising up to 5 halogen atoms (e.g F), such as $CH_3$, $CF_3$, or $CHF_2$;

$C_2$-$C_6$ alkenyl, such as —CH═$CH_2$;

$C_1$-$C_6$ alkoxy optionally comprising up to 3 halogen atoms (e.g. F), such as $OCH_3$, $OCH_3$, $OCF_3$;

$C_1$-$C_3$ alkoxy $C_1$-$C_3$ alkyl, such as 2-methoxy-ethyl;

$C_3$-$C_7$ cycloalkyl, such as cyclopropyl, cyclobutyl;

—C(O)$R^{20}$ wherein $R^{20}$ is selected from $C_1$-$C_3$ alkyl;

—OC(O)$R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl);

—$(CH_2)_m$N($R^{23}$)$R^{24}$ wherein m is 0 or 1, $R^{23}$ is selected from hydrogen, $O_1$—$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxo-thiomorpholine;

—$SR^{27}$ wherein $R^{27}$ is selected from hydrogen and $C_1$-$C_3$ alkyl; and —$S(O)_2R^{28}$ wherein $R^{28}$ is selected from hydrogen and $C_1$-$C_3$ alkyl;

and

B represents a monovalent residue (b)

(b)

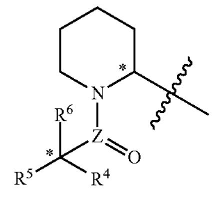

wherein $R^4$, $R^5$ and $R^6$ form together with the carbon atom to which they are attached a hydrocarbon group optionally comprising up to five (e.g. 1, 2, 3, 4) hetero atoms selected from O, N, S, and F (preferably the hydrocarbon group comprises 2 to 15 C-atoms (e.g. 3, 4, 5, 6, 7, 8, 9, 10, 11, 12, 13, or 14 C-atoms); and Z is either C, S or S(O).

The compounds of formula (I) can be generally prepared from compounds of formula (I') as defined herein above (which can be prepared as describe, e.g., in the international patent application PCT/EP2020/079009 (WO 2021/074281)) by reacting them with the respective activated carboxylic acid derivative of type R—C(O)—X (wherein R has the same meaning as provided for formula (I) herein), whereby X is a halogen such as chloride, bromide or fluoride. This reaction may take place in the presence of a base such as an organic base (e.g. triethylamine, diisopropylethylamine) or an inorganic base (e.g. potassium carbonate, potassium phosphate, sodium bicarbonate, sodium hydroxide) in a suitable solvent (e.g. dichloromethane, water, dioxane, N,N-dimethylformamide, tetrahydrofuran) or under solvent-free conditions. The reaction may benefit from addition of a nucleophilic catalyst such as N,N-dimethyl-4-aminopyridine (DMAP). Alternatively, the activated carboxylic acid may be an anhydride of type R—C(O)—O—C(O)—R (wherein R has the same meaning as provided for formula (I) herein) or similar (e.g. a mixed anhydride). Other reagents and conditions for the synthesis of compounds of formula (I) can also be used which are well known to one skilled in the art of organic synthesis.

The invention is now further described with reference to the following non-limiting examples. These examples are for the purpose of illustration only and it is understood that variations and modifications can be made by one skilled in the art.

EXAMPLES

Example A: 2-(methylthio)-1-(2-(5-(p-tolyl)-1H-imidazol-2-yl)piperidin-1-yl)propan-1-one Example Aa: tert-butyl-2-(1 H-imidazol-2-yl)piperidine-1-carboxylate: To a solution of tert-butyl-2-formylpiperidine-1-carboxylate (9.5 g, 35.6 mmol) and glyoxal solution (40% in water, 25.9 g, 178 mmol) in methanol (100 mL) were added dropwise ammonia solution (25% in water, 17.0 g, 249 mmol) at 0° C. The solution was allowed to warm up to rt. (room temperature) and stirred at rt. for 16 h. Then the solution was concentrated under reduced pressure, and the result residue was extracted with ethyl acetate (100 mL*3). Any precipitate was removed by filtration, and the organic phase was washed with saturated aqueous $NaHCO_3$ solution (100 mL) and brine (100 mL). The solution was then concentrated under reduced pressure to give tert-butyl-2-(1H-imidazol-2-yl)piperidine-1-carboxylate (5.2 g, yield: 58%) as white solid. GC/MS (EI): m/z (%): 251 (3) [M*], 195 (4), 178 (10), 150 (20), 134 (13), 122 (5), 95 (100), 82 (10), 57 (21).

Example Ab: tert-butyl-2-(4,5-dibromo-1H-imidazol-2-yl)piperidine-1-carboxylate: N-bromosuccinimide (7.4 g, 41.8 mmol) was added portionwise to a solution of tert-butyl-2-(1H-imidazol-2-yl)piperidine-1-carboxylate (5.0 g, 19.9 mmol) in dichloromethane (100 mL) over 10 min at 0° C. The mixture was stirred at 0° C. for another 2 h and then concentrated by rotary evaporate. The residue was dissolved in ethyl acetate (250 mL), washed with water (100 mL*2) and brine (100 mL), dried with $MgSO_4$, and concentrated to get a very brown residue. The residue was recrystallized by dichloromethane/hexanes (1:1) to get tert-butyl-2-(4,5-dibromo-1H-imidazol-2-yl)piperidine-1-carboxylate (6.0 g, yield: 74%) as white solid. GC/MS (EI): m/z (%): 411 (2) [M*], 409 (4) [M*], 407 (2) [M*], 355 (6), 353 (12), 351 (6), 311 (11), 309 (22), 307 (11), 294 (11), 292 (22), 290 (11), 255 (50), 253 (100), 251 (50), 242 (12), 240 (24), 238 (12), 148 (9), 57 (50).

Example Ac: tert-butyl-2-(5-bromo-1H-imidazol-2-yl)piperidine-1-carboxylate: A suspension of the tert-butyl-2-(4,5-dibromo-1H-imidazol-2-yl)piperidine-1-carboxylate (34.0 g, 90%, 74.8 mmol) and $Na_2SO_3$ (94 g, 748 mmol) in ethanol (300 mL) and water (300 mL) was refluxed overnight. Then cool down and concentrated. The residue was partitioned between $CH_2C_{12}$ (200 mL) and $H_2O$ (200 mL). The aqueous layer was extracted with ethyl acetate (200 mL*3). The combined organic layers were washed with brine (200 mL), dried with $Na_2SO_4$, filtered and evaporated. The residue was purified by column chromatography on silica gel to give tert-butyl-2-(5-bromo-1H-imidazol-2-yl)

piperidine-1-carboxylate (23.0 g, yield: 93%) as white solid. GC/MS (EI): m/z (%): 329 (3) [M*], 331 (3) [M*], 275 (10), 273 (10), 258 (9), 256 (9), 230 (20), 228 (20), 214 (26), 212 (26). 175 (100), 173 (100), 162 (9), 160 (9), 93 (8), 57 (44).

Example Ad: tert-butyl 2-(5-(p-tolyl)-1H-imidazol-2-yl) piperidine-1-carboxylate: A pressure vessel was charged with tert-butyl 2-(5-bromoimidazol-2-yl)piperidine-1-carboxylate (400 mg, 1.211 mmol), p-tolylboronic acid (181 mg, 1.332 mmol, 1.1 equiv.), sodium carbonate (257 mg, 2.42 mmol, 2 equiv.), 1,1'-bis(diphenylphosphino)-ferrocene-palladium(II)dichloride dichloromethane complex (49 mg, 0.061 mmol, 0.05 equiv.), tetrahydrofuran (5 mL) and water (1 mL). The mixture was degassed by purging with nitrogen and the vessel was sealed. The mixture was stirred and heated to 100° C. overnight. The resulting mixture was cooled to 0° C., the vessel was opened and the contents poured into aq. sat. $NaHCO_3$ solution (50 mL), extracted with EtOAc (2×50 mL), washed with water (50 mL) and brine (50 mL), dried over $MgSO_4$ and concentrated under reduced pressure. The crude material was purified by silica gel flash column chromatography eluting with a gradient of EtOAc in Heptane to give tert-butyl 2-(5-(p-tolyl)imidazol-2-yl)piperidine-1-carboxylate (314 mg, 0.920 mmol, 76% yield) as a white solid. MS (El, 70 eV): 341 (4, [M]+•), 285 (11), 268 (3), 240 (30), 185 (100), 172 (16), 91 (6), 57 (99). 1H NMR (DMSO-d6, 400 MHz, mixture of rotamers and tautomers): δ11.66-12.09 (m, 1H), 7.49-7.70 (m, 2H), 7.20-7.48 (m, 1H), 7.08-7.23 (m, 2H), 5.34-5.23 (m, 1H), 3.89 (br d, J=12.1 Hz, 1H), 3.05 (br t, J=10.9 Hz, 1H), 2.28 (s, 3H), 2.18-2.25 (m, 1H), 1.65-1.78 (m, 1H), 1.22-1.63 (m, 13H) ppm. $^{13}C$ NMR (75 MHz, DMSO, mixture of tautomers) δ 155.1 (q), 147.5 (q), 140.2 (q), 135.3 (q), 132.7 (q), 129.4 (t), 124.6 (t), 112.5 (t), 79.3 (q), 63.3 (d), 49.7 (t), 41.2 (d), 28.5 (s), 28.4 (d), 26.8 (d), 25.3 (d), 21.2 (s), 19.9 (d) ppm.

Example Ae: 2-(5-(p-tolyl)-1H-imidazol-2-yl)piperidine: A solution of tert-butyl 2-(5-(p-tolyl)imidazol-2-yl)piperidine-1-carboxylate (304 mg, 0.890 mmol) in dichloromethane (3 mL) was treated dropwise at 5° C. with trifluoroacetic acid (0.549 mL, 7.12 mmol, 8 equiv.) and the resulting mixture stirred at room temperature for 2 hours or until complete consumption of the starting material. The mixture was poured into iced water (30 mL) and the pH made basic by the addition of aqueous 1M NaOH solution. The mixture was then extracted with dichloromethane (3×20 mL), dried over $MgSO_4$ and concentrated under reduced pressure to give 2-(5-(p-tolyl)imidazol-2-yl)piperidine (160 mg, 0.664 mmol, 74% yield) as a pale yellow oil which was used in the next step without further purification. MS (EI, 70 eV): 241 (6, [M]+•), 185 (100), 172 (13), 158 (8), 91 (3), 84 (4). 1H NMR (CHLOROFORM-d, 400 MHz): δ 8.67-8.89 (br s, 1H), 7.50 (d, J=8.1 Hz, 2H), 7.19 (d, J=7.8 Hz, 2H), 7.13 (s, 1H), 4.14 (dd, J=12.3, 3.1 Hz, 1H), 3.30 (br d, J=12.7 Hz, 1H), 2.71-2.84 (m, 1H), 2.37 (s, 3H), 2.15-2.27 (m, 1H), 2.01 (br dd, J=14.4, 3.2 Hz, 1H), 1.90 (br d, J=13.4 Hz, 1H), 1.67-1.77 (m, 2H), 1.32-1.46 ppm (m, 1H).

Example Af: 2-(methylthio)-1-(2-(5-(p-tolyl)imidazol-2-yl)piperidin-1-yl)propan-1-one: To a solution of 2-(5-(p-tolyl)imidazol-2-yl)piperidine (0.88 mmol) in dichloromethane (2 mL) was added HOBt (1.056 mmol, 1.2 equiv.) and 3-(((ethylimino)methylene)amino)-N,N-dimethylpropan-1-amine hydrochloride (1.056 mmol, 1.2 equiv.) at 0-5° C. and the mixture was stirred at room temperature for 0.5 h. The mixture was then treated with 2-(methylthio)propanoic acid (0.968 mmol, 1.1 equiv.) and N,N-diisopropylethylamine (0.88 mmol, 1 equiv.) and the resulting mixture was stirred at rt. for 16 h. The mixture was filtered and solvent was removed and the crude purified by silica gel chromatography (gradient of EtOAc in Heptane) to give 2-(methylthio)-1-(2-(5-(p-tolyl)imidazol-2-yl)piperidin-1-yl)propan-1-one as a white solid. MS (El, 70 eV): 343 (2, [M]+•), 241 (17), 240 (100), 213 (13), 185 (18), 184 (9), 75 (55), 56 (11), 55 (9), 47 (10), 41 (11). $^{1}H$ NMR (400 MHz, DMSO-de, mixture of stereoisomers and tautomers) δ 12.07, 11.99, 11.95, 11.76 (brs, 1H), 7.72-7.60 (m, 2H), 7.59-7.42 (m, 1H), 7.26-7.08 (m, 2H), 5.75-5.39 (m, 1H), 4.49-3.00 (m, 3H), 2.71-2.15 (m, 1H), 2.30 (s, 3H), 2.07-1.96 (m, 3H), 1.94-1.48 (m, 5H), 1.43-1.34 (m, 3H) ppm. $^{13}C$ NMR (101 MHz, DMSO-de, mixture of stereoisomers and tautomers) δ 170.2 (q), 170.2 (q), 170.0 (q), 147.0 (q), 146.8 (q), 146.7 (q), 140.4 (q), 140.3 (q), 139.9 (q), 135.3 (q), 135.2 (q), 135.1 (q), 132.7 (q), 132.6 (q), 132.6 (q), 129.7 (t), 129.3 (t), 124.6 (t), 113.0 (t), 112.6 (t), 112.5 (t), 51.5 (t), 47.3 (t), 47.0 (t), 43.1 (d), 43.0 (d), 38.8 (d), 38.0 (t), 37.6 (t), 37.3 (t), 28.8 (d), 28.6 (d), 28.1 (d), 27.9 (d), 26.1 (d), 25.7 (d), 25.4 (d), 21.2 (s), 20.3 (d), 20.1 (d), 18.3 (s), 18.0 (s), 17.8 (s), 11.9 (s), 11.7 (s), 11.6 (s) ppm.

Example B: 2-methyl-1-(2-(5-(p-tolyl)-1 H-imidazol-2-yl)piperidin-1-yl)butan-1-one Prepared using the same protocol as for Example Af using 2-methylbutanoic acid instead of 2-(methylthio)propanoic acid to give 2-methyl-1-(2-(5-(p-tolyl)-1 H-imidazol-2-yl)piperidin-1-yl)butan-1-one as a white solid. GC/MS (EI): m/z (%): 325 (10) [M*], 268 (2), 240 (100), 224 (3), 185 (10), 159(2), 142 (1), 84 (2), 57 (4). $^{1}H$ NMR (300 MHz, DMSO-$d_6$, mixture of stereoisomers and tautomers) δ 12.05-11.72 (m, 1H), 7.73-7.53 (m, 2H), 7.51-7.40 (m, 1H), 7.27-7.03 (m, 2H), 5.81-5.28 (m, 1H), 4.61-3.16 (m, 2H), 2.87-2.58 (m, 1H), 2.38-2.19 (m, 4H), 1.86-1.49 (m, 5H), 1.46-1.23 (m, 2H), 1.09-0.95 (m, 3H), 0.94-0.80 (m, 3H). $^{13}C$ NMR (75 MHz, DMSO-$d_6$, mixture of stereoisomers and tautomers) δ 175.4 (q), 175.2 (q), 147.3 (q), 147.2 (q), 140.5 (q), 140.1 (q), 135.2 (q), 132.7 (q), 129.7 (t), 129.3 (t), 124.6 (t), 112.9 (t), 112.6 (t), 51.5 (t), 46.9 (t), 46.8 (t), 42.6 (d), 38.6 (d), 36.8 (t), 36.5 (t), 36.1 (t), 29.2 (d), 28.9 (d), 28.4 (d), 27.2 (d), 26.9 (d), 26.2 (d), 25.4 (d), 25.2 (d), 21.2 (s), 20.3 (d), 18.4 (s), 17.7 (s), 17.3 (s), 12.2 (s), 12.0 (s), 11.9 (s) ppm.

Example 1: 1-(2-(1-isobutyryl-4-(p-tolyl)-1H-imidazol-2-yl)piperidin-1-yl)-2-(methylthio)propan-1-one: a solution of 2-(methylthio)-1-(2-(5-(p-tolyl)-1 H-imidazol-2-yl)piperidin-1-yl)propan-1-one (0.2 g, 0.58 mmol, 1.0 equiv.) in Dichloromethane (2 mL) was treated with isobutyryl chloride (0.074 g, 0.70 mmol, 1.2 equiv.). The reaction mixture was stirred for 30 min at ambient temperature and then poured onto iced water (50 mL), extracted with DCM (3×50 mL), washed with water and brine (50 mL each), dried over magnesium sulfate and concentrated. The resulting crude was purified by flash chromatography on silica gel (7-50% EtoAc in Heptane) to give 1-(2-(1-isobutyryl-4-(p-tolyl)-1 H-imidazol-2-yl)piperidin-1-yl)-2-(methylthio)propan-1-one (0.21 g, 0.51 mmol, 87% yield) as an off-white solid.

GC/MS (EI): m/z (%): 413 (3) [$M^+$], 398 (4), 367 (6), 343 (4), 338 (5), 268 (37), 240 (100). $^{13}C$ NMR (101 MHz, DMSO-$d_6$): δ=176.7, 176.2, 171.5, 170.8, 170.6, 151.5, 151.4, 150.5, 139.5, 137.2, 137.1, 137.0, 130.6, 130.5, 130.4, 129.6, 129.6, 129.4, 125.3, 125.2, 124.6, 114.5, 114.0, 113.8, 60.2, 51.1, 48.1, 47.9, 44.2, 43.7, 42.2, 38.5, 38.3, 37.4, 34.7, 34.5, 28.9, 28.4, 28.1, 25.6, 25.3, 21.3, 21.2, 19.5, 19.5, 19.5, 19.4, 19.4, 19.1, 18.1, 17.9, 17.7, 17.3, 15.5, 14.5, 12.2, 12.1, 11.3.

Example 2: 1-(2-(1-acetyl-4-(p-tolyl)-1 H-imidazol-2-yl) piperidin-1-yl)-2-(methylthio)propan-1-one: Prepared analogously to Example 1, from 2-(methylthio)-1-(2-(5-(p-tolyl)imidazol-2-yl)piperidin-1-yl)propan-1-one and acetyl chloride to give the title compound as an off-white solid.

GC/MS (EI): m/z (%): 385 (7) [$M^+$], 370 (2), 339 (19), 268 (36), 240 (100). $^{13}C$ NMR (101 MHz, DMSO-$d_6$): δ=171.5, 170.8, 170.6, 170.0, 169.5, 151.3, 139.2, 137.1, 137.0, 130.5, 130.5, 129.7, 129.6, 125.2, 125.1, 115.4, 114.9, 114.7, 60.2, 51.0, 48.1, 47.9, 44.3, 43.8, 38.5, 38.2, 37.4, 31.7, 28.8, 28.3, 28.0, 25.6, 25.3, 25.2, 25.1, 22.6, 21.3, 21.2, 19.4, 18.1, 17.9, 17.7, 14.6, 14.4, 12.2, 12.1, 11.3.

Example 3: 1-(2-(1-propionyl-4-(p-tolyl)-1 H-imidazol-2-yl)piperidin-1-yl)propan-1-one: a)

To a solution tert-butyl 2-(5-(p-tolyl)-1H-imidazol-2-yl) piperidine-1-carboxylate (7.6 g, 20.03 mmol) in dichloromethane (200 mL) was added 2,2,2-trifluoroacetic acid (18.3 g, 160 mmol) at 5° C., and the mixture was stirred at rt. for 2 h. The completion of reaction was monitored by TLC. The reaction solution was cooled to room temperature and saturated $NaHCO_3$ solution (200 mL) was added, extracted with EA (100 mL*3) and the organic phase was concentrated to give 2-(5-(2,4-difluorophenyl)-1H-imidazol-2-yl)piperidine as a yellow solid (4.9 g, yield: 91%).

b) To a solution of 2-(5-(p-tolyl)-1H-imidazol-2-yl)piperidine (300 mg, 1.243 mmol) and triethylamine (189 mg, 1.865 mmol) in dichloromethane (30 ml) was added propionyl chloride (138 mg, 1.492 mmol) at 0~5° C. and the mixture was stirred at rt for 6 h. The mixture was filtered and solvent was removed and purified by silica gel chromatography (hexane: EA=2:1) to give 1-(2-(3-propionyl-5-(p-tolyl)imidazol-2-yl)piperidin-1-yl)propan-1-one (165 mg, yield 38%) as white solid.

GC/MS (EI): m/z (%): 353 (2) [$M^+$], 296 (3), 280 (20), 240 (100), 224 (16), 185 (26), 130 (4), 117 (6), 84 (4). $^1H$ NMR (300 MHz, DMSO-$d_6$) δ 8.29-8.06 (m, 1H), 7.84-7.62 (m, 2H), 7.32-7.13 (m, 2H), 6.22-5.86 (m, 1H), 4.55-3.59 (m, 2H), 3.18-2.94 (m, 2H), 2.46-2.21 (m, 5H), 2.31 (s, 3H), 2.10-1.25 (m, 6H), 1.19-1.09 (m, 3H), 1.01-0.89 (m, 3H). $^{13}C$ NMR (75 MHz, DMSO-$d_6$) δ 173.6 (q), 173.3 (q), 172.7 (q), 151.5 (q), 150.7 (q), 139.5 (q), 139.3 (q), 137.0 (q), 130.4 (q), 130.3 (q), 129.6 (t), 125.2 (t), 114.3 (t), 113.8 (t), 51.0 (t), 47.5 (t), 43.4 (d), 29.7 (d), 28.9 (d), 28.1 (d), 26.7 (d), 26.2 (d), 25.5 (d), 25.0 (d), 21.2 (s), 19.4 (d), 19.3 (d), 9.8 (s), 9.6 (s), 8.6 (s), 8.5 (s) ppm.

Example 4: 1-(2-(1-isobutyryl-4-(p-tolyl)-1H-imidazol-2-yl)piperidin-1-yl)-2-methylpropan-1-one: Following an analogous procedure as in Example 3, 2-(5-(p-tolyl)-1H-imidazol-2-yl)piperidine (300 mg, 1.243 mmol), isobutyryl chloride (159 mg, 1.492 mmol) and triethylamine (189 mg, 1.865 mmol) in dichloromethane (30 ml) were reacted to give the title product (140 mg, yield: 29%) as white solid.

GC/MS (EI): m/z (%): 381 (2) [$M^+$], 310 (13), 294 (19), 240 (100), 224 (18), 185 (26), 159 (4), 130 (3), 117 (5), 71 (9). $^1H$ NMR (300 MHz, DMSO-$d_6$) δ 8.38-8.17 (m, 1H), 7.73 (d, J=7.5 Hz, 2H), 7.21 (d, J=7.5 Hz, 2H), 6.16-5.95 (m, 1H), 4.56-3.83 (m, 2H), 3.08-2.58 (m, 1H), 2.30 (s, 3H), 2.12-1.28 (m, 7H), 1.28-1.12 (m, 6H), 1.08-0.67 (m, 6H). $^{13}C$ NMR (75 MHz, DMSO-$d_6$) δ 176.5 (q), 176.1 (q), 151.7 (q), 139.5 (q), 137.1 (q), 130.5 (q), 129.6 (t), 125.2 (t), 113.7 (t), 47.7 (t), 43.4 (d), 34.5 (t), 29.9 (t), 28.1 (d), 25.7 (d), 21.2 (s), 19.8 (s), 19.5 (d), 19.4 (s), 19.4 (s), 18.9 (s) ppm.

Example 5: 2-(methylthio)-1-(2-(1-(2-(methylthio)propanoyl)-4-(p-tolyl)-1H-imidazol-2-yl)piperidin-1-yl)propan-1-one: A solution of 2-(5-(p-tolyl)-1H-imidazol-2-yl) piperidine (2.1 g, 8.7 mmol, 1.0 equiv.) in dichloromethane (DCM) (15 mL) at 0° C. was treated with triethylamine (1.82 mL, 13.1 mmol, 1.5 equiv.) followed by dropwise addition of 2-(methylthio)propanoyl chloride (1.33 g, 9.59 mmol, 1.1 equiv.). The mixture was stirred for 13 h and then poured onto iced 1 M aq. HCl (50 mL), extracted with EtOAc (3×50 mL), washed with sat. aq. $NaHCO_3$(50 mL), water (50 mL), brine (50 mL), dried over magensium sulfate and concentrated. The crude material was purified by flash chromatography on silica gel (7-80% EtOAc in Heptane) to give 2-(methylthio)-1-(2-(1-(2-(methylthio)propanoyl)-4-(p-tolyl)-1 H-imidazol-2-yl)piperidin-1-yl)propan-1-one (1.96 g, 4.4 mmol, 50% yield) as a yellow wax.

DIP/MS (EI): m/z (%): 370 (1) [$M^+$—$C_3$H7S], 268 (5), 240 (26), 185 (14), 75 (100) [$C_3$H7S+]. 1H NMR (400 MHz, CHLOROFORM-d, 25° C.): δ=7.63-7.76 (m, 2H), 7.52-7.62 (m, 1H), 7.15-7.25 (m, 2H), 5.87-6.56 (m, 1H), 4.22-4.76 (m, 1H), 3.88-4.15 (m, 2H), 3.65-3.81 (m, 1H), 2.38 (s, 3H), 2.07-2.18 (m, 4H), 1.22-1.76 (m, 10H), 0.84-0.98 ppm (m, 4H).

Example 6: 1-(2-(1-benzoyl-4-(p-tolyl)-1 H-imidazol-2-yl)piperidin-1-yl)-2-(methylthio)propan-1-one: A solution of 2-(methylthio)-1-(2-(5-(p-tolyl)-1 H-imidazol-2-yl)piperidin-1-yl)propan-1-one (0.2 g, 0.582 mmol) in Dichloromethane (2 mL) at ambient temperature was treated with benzoyl chloride (0.098 g, 0.699 mmol). The reaction mixture was stirred for 2 h at ambient temperature and then poured into iced water, extracted with DCM (3×25 mL), washed with water (25 mL) and brine (25 mL), dried over magnesium sulfate and concentrated. The crude material was purified by flash chromatography on silica gel (7-60% EtOAc in Heptane) to give 1-(2-(1-benzoyl-4-(p-tolyl)-1H-imidazol-2-yl)piperidin-1-yl)-2-(methylthio)propan-1-one (0.13 g, 0.290 mmol, 50% yield) as a yellow oily wax.

DIP/MS (EI): m/z (%): 447 (1) [$M^+$], 432 (1), 401 (1), 372 (2), 344 (4), 240 (35), 105 (100), 75 (32). 1H NMR (400 MHz, DMSO-$d_6$, 25°C.): δ=7.69-8.11 (m, 6H), 7.48-7.68 (m, 2H), 7.11-7.27 (m, 2H), 5.73-6.36 (m, 1H), 3.73-4.09 (m, 3H), 2.31 (s, 3H), 1.94-2.13 (m, 4H), 1.75-1.88 (m, 2H), 1.62 (br s, 2H), 1.13-1.41 ppm (m, 4H).

Example 7: N-(1-benzoyl-1H-pyrazol-3-yl)-N-(thiophen-2-ylmethyl)-2-(p-tolyloxy)acetamide: A solution of N-(1H-pyrazol-3-yl)-N-(thiophen-2-ylmethyl)-2-(p-tolyloxy)acetamide (0.150 g, 0.458 mmol) and triethylamine (0.056 g, 0.550 mmol) in Dichloromethane (3 mL) was treated with benzoyl chloride (0.077 g, 0.550 mmol) at 5° C. The cooling bath was removed and the reaction mixture was stirred at ambient temperature for 2 h and then poured into iced water, extracted with DCM (3×25 mL), washed with water (25 mL) and brine (25 mL), dried over magnesium sulfate and concentrated. The crude material was purified by flash chromatography on silica gel (7-30% EtOAc in Heptane) to give N-(1-benzoyl-1 H-pyrazol-3-yl)-N-(thiophen-2-ylmethyl)-2-(p-tolyloxy)acetamide (0.17 g, 0.394 mmol, 86% yield) as a white solid.

DIP/MS (EI): m/z (%): 431 (1) [$M^+$], 324 (2), 282 (2), 121 (5), 105 (100), 97 (57), 91 (18), 77 (37). 1H NMR (400 MHz, DMSO-d6, 25° C.): δ=8.61 (d, J=2.9 Hz, 1H), 7.77-8.03 (m, 2H), 7.65-7.73 (m, 1H), 7.50-7.58 (m, 2H), 7.39-7.47 (m, 1H), 7.04 (d, J=8.3 Hz, 3H), 6.83-6.99 (m, 2H), 6.61-6.77 (m, 2H), 5.06-5.35 (m, 2H), 4.49-5.05 (m, 2H), 2.19-2.25 ppm (m, 3H).

Example 8: N-(1-isobutyryl-1H-pyrazol-3-yl)-N-(thiophen-2-ylmethyl)-2-(p-tolyloxy)acetamide: A solution of N-(1H-pyrazol-3-yl)-N-(thiophen-2-ylmethyl)-2-(p-tolyloxy)acetamide (0.15 g, 0.458 mmol) and triethylamine (0.056 g, 0.550 mmol) in Dichloromethane (3 mL) was treated with isobutyryl chloride (0.059 g, 0.550 mmol) at 5° C. The cooling bath was removed and the reaction mixture was stirred at ambient temperature for 2 h and then poured into iced water, extracted with DCM (3×25 mL), washed with water (25 mL) and brine (25 mL), dried over magnesium sulfate and concentrated. The crude material was purified by flash chromatography on silica gel (7-30% EtOAc in Heptane) to give N-(1-isobutyryl-1H-pyrazol-3-yl)-N-(thiophen-2-ylmethyl)-2-(p-tolyloxy)acetamide (0.175 g, 0.440 mmol, 96% yield) as a colorless liquid.

GC/MS (EI): m/z (%): 397 (7) [$M^+$], 327 (1), 290 (2), 220 (29), 178 (21), 121 (8), 97 (100), 71 (15), 43 (33). 1H NMR (400 MHz, DMSO-d6, 25° C.): δ=8.41 (d, J=2.9 Hz, 1H), 7.44 (dd, J=5.0, 1.1 Hz, 1H), 7.01-7.11 (m, 3H), 6.95 (br dd, J=4.9, 3.7 Hz, 1H), 6.77-6.90 (m, 1H), 6.68-6.76 (m, 2H), 5.10-5.32 (m, 2H), 4.98 (br s, 2H), 3.67 (dt, J=13.3, 6.5 Hz, 1H), 2.22 (s, 3H), 1.18 ppm (d, J=6.8 Hz, 6H)

Example 9: N-(1-acetyl-1H-pyrazol-3-yl)-N-(thiophen-2-ylmethyl)-2-(p-tolyloxy)acetamide: A solution of N-(1H-pyrazol-3-yl)-N-(thiophen-2-ylmethyl)-2-(p-tolyloxy)acetamide (0.15 g, 0.458 mmol) and triethylamine (0.056 g, 0.550 mmol) in Dichloromethane (3 mL) was treated with acetyl chloride (0.043 g, 0.550 mmol) at 5° C. The cooling bath was removed and the reaction mixture was stirred at ambient temperature for 2 h and then poured into iced water, extracted with DCM (3×25 mL), washed with water (25 mL) and brine (25 mL), dried over magnesium sulfate and concentrated. The crude material was purified by flash chromatography on silica gel (7-30% EtOAc in Heptane) to give N-(1-acetyl-1H-pyrazol-3-yl)-N-(thiophen-2-ylmethyl)-2-(p-tolyloxy)acetamide (0.140 g, 0.379 mmol, 83% yield) as a white solid. GC/MS (EI): m/z (%): 369 (8) [$M^+$], 262 (6), 220 (35), 178 (23), 97 (100), 43 (15). 1H NMR (400 MHz, CHLOROFORM-d, 25° C.): δ=8.21 (d, J=2.7 Hz, 1H), 7.25 (dd, J=5.1, 1.2 Hz, 1H), 7.07 (d, J=8.3 Hz, 2H), 7.01 (br s, 1H), 6.95 (dd, J=5.0, 3.5 Hz, 1H), 6.75 (br d, J=8.1 Hz, 2H), 6.14-6.56 (m, 1H), 5.06-5.43 (m, 2H), 4.87 (s, 2H), 2.58-2.68 (m, 3H), 2.29 ppm (s, 3H).

Example 10: 1-(2-(1-((1R,2S,5R)-2-isopropyl-5-methylcyclohexane-1-carbonyl)-4-(p-tolyl)-1H-imidazol-2-yl)piperidin-1-yl)-2-(methylthio)propan-1-one: A solution of 2-(methylthio)-1-(2-(5-(p-tolyl)-1H-imidazol-2-yl)piperidin-1-yl)propan-1-one (1 g, 2.91 mmol) and ethyldi(isopropyl)amine (DIPEA) (0.508 mL, 2.91 mmol) in Dichloromethane (5 mL) was treated with a solution of (1R,2S,5R)-2-isopropyl-5-methylcyclohexane-1-carbonyl chloride (0.590 g, 2.91 mmol) in Dichloromethane (5 mL) at 5° C. The cooling bath was removed and the reaction mixture was stirred at ambient temperature for overnight and then poured into iced 1M aq. HCl (5 mL), extracted with DCM (3×25 mL), washed with 1M aq. NaOH (10 mL), water (25 mL) and brine (25 mL), dried over magnesium sulfate and concentrated. The crude material was purified by flash chromatography on silica gel (7-30% EtOAc in Heptane) to give 1-(2-(1-((1R,2S,5R)-2-isopropyl-5-methylcyclohexane-1-carbonyl)-4-(p-tolyl)-1H-imidazol-2-yl)piperidin-1-yl)-2-(methylthio)propan-1-one (1.1 g, 2.158 mmol, 74% yield) as a yellow viscous liquid. DIP/MS (EI): m/z (%): 509 (2) [$M^+$], 463 (2), 434 (1), 342 (9), 296 (6), 268 (23), 240 (100), 75 (27). 1H NMR (400 MHz, DMSO-d6, 25° C.): δ=8.39-8.56 (m, 1H), 7.64-7.89 (m, 2H), 7.09-7.40 (m, 2H), 5.90-6.37 (m, 1H), 3.76-4.28 (m, 3H), 3.21-3.49 (m, 3H), 2.32 (s, 3H), 2.13 (td, J=11.6, 3.4 Hz, 1H), 1.83-2.07 (m, 4H), 1.53-1.82 (m, 13H), 1.22-1.42 (m, 7H), 1.03-1.21 (m, 4H), 0.84-0.93 (m, 13H), 0.69-0.81 ppm (m, 5H).

Example 11: 1-(2-(1-acetyl-4-(p-tolyl)-1H-imidazol-2-yl) piperidin-1-yl)-2-methylbutan-1-one: A solution of 2-methyl-1-(2-(5-(p-tolyl)-1H-imidazol-2-yl)piperidin-1-yl) butan-1-one (0.5 g, 1.536 mmol) and DIPEA (0.295 mL, 1.690 mmol) in Dichloromethane (5 mL) was treated with a solution of acetyl chloride (0.120 mL, 1.690 mmol) in Dichloromethane (5 mL) at 5° C. After the addition the cooling bath was removed and the reaction mixture was stirred overnight at ambient temperature and then poured into iced 1M aq. HCl (5 mL), extracted with DCM (3×25 mL), washed with 1M aq. NaOH (10 mL), water (25 mL) and brine (25 mL), dried over magnesium sulfate and concentrated. The crude material was purified by flash chromatography on silica gel (7-30% EtOAc in Heptane) to give 1-(2-(1-acetyl-4-(p-tolyl)-1 H-imidazol-2-yl)piperidin-1-yl)-2-methylbutan-1-one (0.30 g, 0.816 mmol, 53% yield) as a white solid. GC/MS (EI): m/z (%): 367 (5) [$M^+$], 324 (1), 282 (2), 240 (100), 43 (42). 1H NMR (400 MHz, DMSO-d6, 25°C.): δ=8.09-8.22 (m, 1H), 7.72 (d, J=8.1 Hz, 2H), 7.22 (br d, J=7.8 Hz, 2H), 5.86-6.24 (m, 1H), 3.60-4.54 (m, 2H), 2.73-2.92 (m, 1H), 2.62-2.71 (m, 3H), 2.26-2.43 (m, 3H), 1.91-1.99 (m, 1H), 1.66-1.89 (m, 2H), 1.22-1.64 (m, 5H), 0.92-1.05 (m, 3H), 0.69-0.90 (m, 3H), 0.43 ppm (t, J=7.3 Hz, 1H). 13C NMR (101 MHz, DMSO-d6, 25° C.): δ=176.3, 175.9, 169.4, 151.6, 151.5, 139.2, 139.2, 137.0, 137.0, 130.6, 129.6, 129.6, 125.2, 125.1, 125.1, 120.0, 114.7, 60.2, 47.8, 47.7, 43.6, 43.5, 36.7, 36.4, 28.1, 28.0, 27.0, 26.9, 25.8, 25.1, 21.3, 21.2, 19.6, 17.8, 16.8, 14.5, 12.2, 11.8 ppm.

Example 12: 1-(2-(1-isobutyryl-4-(p-tolyl)-1 H-imidazol-2-yl)piperidin-1-yl)-2-methylbutan-1-one: A solution of 2-methyl-1-(2-(5-(p-tolyl)-1H-imidazol-2-yl)piperidin-1-yl) butan-1-one (0.5 g, 1.536 mmol) and DIPEA (0.295 mL, 1.690 mmol) in Dichloromethane (5 mL) was treated with a solution of isobutyryl chloride (0.180 g, 1.690 mmol) in Dichloromethane (5 mL) at 5° C. After the addition the cooling bath was removed and the reaction mixture was stirred for 2 h at ambient temperature and then poured into iced 1M aq. HCl (5 mL), extracted with DCM (3×25 mL), washed with 1M aq. NaOH (10 mL), water (25 mL) and brine (25 mL), dried over magnesium sulfate and concentrated. The crude material was purified by flash chromatography on silica gel (1-30% EtOAc in Heptane) to give 1-(2-(1-isobutyryl-4-(p-tolyl)-1H-imidazol-2-yl)piperidin-1-yl)-2-methylbutan-1-one (0.13 g, 0.329 mmol, 21% yield) as a white solid. DIP/MS (EI): m/z (%): 395.3 (10) [M*], 352.3 (1), 324.2 (4), 240.2 (100), 185.2 (38), 71.2 (16), 57.1 (44), 43.1 (96). 1H NMR (400 MHz, DMSO-d6, 25° C.): δ=8.23-8.38 (m, 1H), 7.74 (br d, J=7.8 Hz, 2H), 7.17-7.25 (m, 2H), 5.87-6.21 (m, 1H), 3.92-4.51 (m, 2H), 3.44-3.70 (m, 1H), 2.73-2.90 (m, 1H), 2.25-2.42 (m, 3H), 1.66-1.98 (m, 3H), 1.27-1.64 (m, 5H), 1.23 (t, J=6.7 Hz, 6H), 0.91-1.08 (m, 3H), 0.67-0.87 (m, 3H), 0.43 ppm (br t, J=7.2 Hz, 1H).

Example 13: 1-(2-(1-((1R,2S,5R)-2-isopropyl-5-methylcyclohexane-1-carbonyl)-4-(p-tolyl)-1H-imidazol-2-yl)piperidin-1-yl)-2-methylbutan-1-one: A solution of 2-methyl-1-(2-(5-(p-tolyl)-1H-imidazol-2-yl)piperidin-1-yl)butan-1-one (2 g, 6.15 mmol) and DIPEA (1.073 mL, 6.15 mmol) in Dichloromethane (15 mL) was treated with a solution of (1R,2S,5R)-2-isopropyl-5-methylcyclohexane-1-carbonyl chloride (1.246 g, 6.15 mmol) in Dichloromethane (5 mL) at 5° C. The cooling bath was removed and the reaction mixture was stirred at ambient temperature for overnight. Thin Layer Chromatography (TLC) analysis showed remainig starting material. N,N-dimethyl-4-aminopyridine (DMAP) (0.1 g, 0.81 mmol) was added and the reaction mixture was stirred for 3 h at ambient temperature and then poured into iced 1M aq. HCl (15 mL), extracted with DCM (3×75 mL), washed with 1M aq. NaOH (30 mL), water (75 mL) and brine (75 mL), dried over magnesium sulfate and concentrated. The crude material was purified by flash chromatography on silica gel (7-30% EtOAc in Heptane) to give 1-(2-(1-((1R,2S,5R)-2-isopropyl-5-methylcyclohexane-1-carbonyl)-4-(p-tolyl)-1H-imidazol-2-yl)piperidin-1-yl)-2-methylbutan-1-one (2.8 g, 5.69 mmol, 93% yield) as a white solid. DIP/MS (El): m/z (%): 491 (2) [M*], 448 (1), 406 (1), 324 (10), 240 (100), 185 (93), 43 (12). 1H NMR (400 MHz, DMSO-d6, 25° C.): δ=8.41-8.55 (m, 1H), 7.75 (br d, J=7.8 Hz, 2H), 7.18-7.27 (m, 2H), 5.78-6.26 (m, 1H), 3.94-4.50 (m, 2H), 3.25-3.73 (m, 4H), 2.73-2.90 (m, 1H), 2.36 (br dd, J=11.6, 3.3 Hz, 1H), 1.51-1.98 (m, 13H), 1.22-1.50 (m, 6H), 0.63-1.16 ppm (m, 25H).

Example 14: 1-(2-(1-(2-methoxyacetyl)-4-(p-tolyl)-1H-imidazol-2-yl)piperidin-1-yl)-2-methylbutan-1-one: A solution of 2-methyl-1-(2-(5-(p-tolyl)-1H-imidazol-2-yl)piperidin-1-yl)butan-1-one (2 g, 6.15 mmol), DMAP (0.075 g, 0.615 mmol) and triethylamine (TEA) (0.942 mL, 6.76 mmol) in Dichloromethane (10 mL) was treated with a solution of 2-methoxyacetyl chloride (0.734 g, 6.76 mmol) in Dichloromethane (10 mL) at 5° C. After the addition the cooling bath was removed and the reaction mixture was stirred at ambient temperature for overnight. TLC analysis showed about 50% conversion. The reaction mixture was treated with 2-methoxyacetyl chloride (0,4 g, 3.69 mmol) and was stirred for further 3 h at ambient temperature and then poured into iced 1M aq. HCl (15 mL), extracted with DCM (3×75 mL), washed with 1M aq. NaOH (30 mL), water (75 mL) and brine (75 mL), dried over magnesium sulfate and concentrated. The crude material was purified by flash chromatography on silica gel (1-30% EtOAc in Heptane) to give 1-(2-(1-(2-methoxyacetyl)-4-(p-tolyl)-1H-imidazol-2-yl)piperidin-1-yl)-2-methylbutan-1-one (1.70 g, 4.28 mmol, 70% yield) as a white solid. DIP/MS (El): m/z (%): 397 (5) [$M^+$], 352 (5), 324 (2), 312 (13), 240 (49), 84 (50), 45 (100). 1H NMR (400 MHz, DMSO-d6, 25° C.): δ=8.00-8.13 (m, 1H), 7.67-7.76 (m, 2H), 7.18-7.27 (m, 2H), 5.90-6.25 (m, 1H), 4.68-4.83 (m, 2H), 3.63-4.53 (m, 2H), 3.44 (s, 3H), 2.75-2.92 (m, 1H), 2.32 (s, 3H), 1.93-2.05 (m, 1H), 1.69-1.91 (m, 2H), 1.23-1.64 (m, 5H), 0.40-1.07 ppm (m, 6H).

Example 15: 1-(2-(1-(2-(benzyloxy)acetyl)-4-(p-tolyl)-1H-imidazol-2-yl)piperidin-1-yl)-2-methylbutan-1-one: A solution of 2-methyl-1-(2-(5-(p-tolyl)-1H-imidazol-2-yl)piperidin-1-yl)butan-1-one (2 g, 6.15 mmol), DMAP (0.075 g, 0.615 mmol) and TEA (0.942 mL, 6.76 mmol) in Dichloromethane (10 mL) was treated with a solution of 2-(benzyloxy)acetyl chloride (1.248 g, 6.76 mmol) in Dichloromethane (10 mL) at 5° C. After the addition the cooling bath was removed and the reaction mixture was stirred at ambient temperature for overnight. TLC showed remaining starting material so additional 2-(benzyloxy)acetyl chloride (0.5 g, 2.71 mmol) was added and the reaction mixture was stirred for further 3 h at ambient temperature and then poured into iced 1M aq. HCl (15 mL), extracted with DCM (3×75 mL), washed with 1M aq. NaOH (30 mL), water (75 mL) and brine (75 mL), dried over magnesium sulfate and concentrated. The crude material was purified by flash chromatography on silica gel (1-30% EtOAc in Heptane) to give 1-(2-(1-(2-(benzyloxy)acetyl)-4-(p-tolyl)-1H-imidazol-2-yl)piperidin-1-yl)-2-methylbutan-1-one (2.70 g, 5.70 mmol, 93% yield) as a white solid.

DIP/MS (El): m/z (%): 473 (6) [$M^+$], 388 (7), 382 (5), 352 (9), 324 (6), 240 (62), 91 (100), 57 (32). 1H NMR (400 MHz, CHLOROFORM-d, 25° C.): δ=7.60-7.71 (m, 2H), 7.32-7.47 (m, 6H), 7.19 (d, J=7.8 Hz, 2H), 5.96-6.47 (m, 1H), 4.49-4.81 (m, 4H), 4.13-4.37 (m, 1H), 3.87-4.13 (m, 1H), 2.68-2.87 (m, 1H), 2.38 (s, 3H), 2.03-2.15 (m, 1H), 1.81-2.02 (m, 2H), 1.63-1.80 (m, 2H), 1.35-1.59 (m, 2H), 0.53-1.21 ppm (m, 6H).

Example 16: 1-(2-(1-(2-(methylthio)propanoyl)piperidin-2-yl)-4-(p-tolyl)-1H-imidazol-1-yl)dodecan-1-one: A solution of 2-(methylthio)-1-(2-(5-(p-tolyl)-1 H-imidazol-2-yl) piperidin-1-yl)propan-1-one (1.5 g, 4.37 mmol), DMAP (0.053 g, 0.437 mmol) and DIPEA (1.068 mL, 6.11 mmol) in Dichloromethane (10 mL) was treated with a solution of dodecanoyl chloride (1.146 g, 5.24 mmol) in Dichloromethane (10 mL) at 5° C. The cooling bath was removed and the reaction mixture was stirred for overnight at ambient temperature and then poured into iced 1M aq. HCl (25 mL), extracted with DCM (3×75 mL), washed with 1M aq. NaOH (50 mL), water (75 mL) and brine (75 mL), dried over magnesium sulfate and concentrated. The crude material was purified by flash chromatography on silica gel (7-30% EtOAc in Heptane) to give 1-(2-(1-(2-(methylthio)propanoyl)piperidin-2-yl)-4-(p-tolyl)-1H-imidazol-1-yl)dodecan-1-one (1.1 g, 2.09 mmol, 48% yield) as an off-white solid.

DIP/MS (EI): m/z (%): 525 (3) [$M^+$], 510 (1), 479 (3), 450 (2), 422 (1), 240 (93), 185 (100), 75 (28). 1H NMR (400 MHz, DMSO-d6, 25° C.): δ=8.14-8.28 (m, 1H), 7.69-7.78 (m, 2H), 7.16-7.25 (m, 2H), 5.89-6.28 (m, 1H), 4.11-4.52 (m, 1H), 3.47-4.11 (m, 3H), 2.93-3.12 (m, 2H), 2.31 (d, J=2.7 Hz, 3H), 2.02-2.28 (m, 2H), 1.89-1.98 (m, 1H), 1.44-1.76 (m, 6H), 1.21-1.40 (m, 25H), 0.81-0.90 ppm (m, 4H).

Example 17: 1-(2-(1-(2-methylbutanoyl)piperidin-2-yl)-4-(p-tolyl)-1H-imidazol-1-yl)dodecan-1-one: A solution of 2-methyl-1-(2-(5-(p-tolyl)-1H-imidazol-2-yl)piperidin-1-yl) butan-1-one (1.5 g, 4.61 mmol), DMAP (0.056 g, 0.461 mmol) and DIPEA (1.127 mL, 6.45 mmol) in Dichloromethane (10 mL) was treated with a solution of dodecanoyl chloride (1.210 g, 5.53 mmol) in Dichloromethane (10 mL) at 5° C. The cooling bath was removed and the reaction mixture was stirred for overnight at ambient temperature and then poured into iced 1M aq. HCl (25 mL), extracted with DCM (3×75 mL), washed with 1M aq. NaOH (50 mL), water (75 mL) and brine (75 mL), dried over magnesium sulfate and concentrated. The crude material was purified by flash chromatography on silica gel (7-30% EtOAc in Heptane) to give 1-(2-(1-(2-methylbutanoyl)piperidin-2-yl)-4-(p-tolyl)-1H-imidazol-1-yl)dodecan-1-one (1.75 g, 3.45 mmol, 75% yield) as a white solid.

DIP/MS (EI): m/z (%): 507 (5) [$M^+$], 422 (1), 240 (100), 185 (26), 57 (20). 1H NMR (400 MHz, DMSO-d6, 25° C.): δ=8.13-8.29 (m, 1H), 7.69-7.77 (m, 2H), 7.14-7.26 (m, 2H), 5.88-6.25 (m, 1H), 3.58-4.54 (m, 2H), 2.93-3.13 (m, 2H), 2.72-2.89 (m, 1H), 2.31 (s, 3H), 1.95 (br d, J=13.0 Hz, 1H), 1.60-1.84 (m, 4H), 1.41-1.59 (m, 3H), 1.21-1.40 (m, 19H), 0.37-1.06 ppm (m, 10H).

Example 18: 1-(2-(1-(2-(methylthio)propanoyl)piperidin-2-yl)-4-(p-tolyl)-1H-imidazol-1-yl)hexan-1-one: A solution of 2-(methylthio)-1-(2-(5-(p-tolyl)-1H-imidazol-2-yl)piperidin-1-yl)propan-1-one (2 g, 5.82 mmol), DMAP (0.071 g, 0.582 mmol) and DIPEA (1.525 mL, 8.73 mmol) in Dichloromethane (10 mL) was treated with a solution of hexanoyl chloride (1.176 g, 8.73 mmol) in Dichloromethane (10 mL) at 5° C. The cooling bath was removed and the reaction mixture was stirred for overnight at ambient temperature and then poured into iced 1M aq. HCl (25 mL), extracted with DCM (3×75 mL), washed with 1M aq. NaOH (50 mL), water (75 mL) and brine (75 mL), dried over magnesium sulfate and concentrated. The crude material was purified by flash chromatography on silica gel (7-30% EtOAc in Heptane) to give 1-(2-(1-(2-(methylthio)propanoyl)piperidin-2-yl)-4-(p-tolyl)-1H-imidazol-1-yl)hexan-1-one (2.2 g, 4.98 mmol, 86% yield) as a white solid.

DIP/MS (EI): m/z (%): 441 (5) [M*], 426 (2), 395 (5), 366 (4), 240 (80), 185 (100), 99 (16), 75 (44), 43 (66). 1H NMR (400 MHz, DMSO-d6, 25° C.): δ=8.15-8.29 (m, 1H), 7.69-7.79 (m, 2H), 7.14-7.25 (m, 2H), 5.90-6.32 (m, 1H), 3.49-4.52 (m, 3H), 2.93-3.14 (m, 2H), 2.15-2.50 (m, 4H), 1.86-2.06 (m, 3H), 1.45-1.82 (m, 8H), 1.20-1.42 (m, 11H), 0.83-0.96 ppm (m, 5H).

Example 19: 1-(2-(1-(2-methylbutanoyl)piperidin-2-yl)-4-(p-tolyl)-1H-imidazol-1-yl)hexan-1-one: A solution of 2-methyl-1-(2-(5-(p-tolyl)-1 H-imidazol-2-yl)piperidin-1-yl)butan-1-one (1.5 g, 4.61 mmol), DMAP (0.056 g, 0.461 mmol) and DIPEA (1.127 mL, 6.45 mmol) in Dichloromethane (10 mL) was treated with a solution of hexanoyl chloride (0.869 g, 6.45 mmol) in Dichloromethane (10 mL) at 5° C. The cooling bath was removed and the reaction mixture was stirred for overnight at ambient temperature and then poured into iced 1M aq. HCl (25 mL), extracted with DCM (3×75 mL), washed with 1M aq. NaOH (50 mL), water (75 mL) and brine (75 mL), dried over magnesium sulfate and concentrated. The crude material was purified by flash chromatography on silica gel (7-30% EtOAc in Heptane) to give 1-(2-(1-(2-methylbutanoyl)piperidin-2-yl)-4-(p-tolyl)-1H-imidazol-1-yl)hexan-1-one (1.85 g, 4.37 mmol, 95% yield) as a white solid.

DIP/MS (El): m/z (%): 423 (5) [M*], 338 (2), 240 (100), 185 (52), 99 (6), 57 (10). 1H NMR (400 MHz, DMSO-d6, 25° C.): δ=8.12-8.31 (m, 1H), 7.67-7.78 (m, 2H), 7.13-7.30 (m, 2H), 5.87-6.26 (m, 1H), 3.56-4.55 (m, 2H), 2.73-3.14 (m, 3H), 2.14-2.49 (m, 4H), 1.62-2.01 (m, 5H), 1.21-1.61 (m, 14H), 0.38-1.06 ppm (m, 12H).

Example 20: Assay on TRPM8 modulators

A HEK293 cell line stably expressing hTRPM8 was generated according to Klein et al., (Chem. Senses 36: 649-658, 2011) and receptor activation was monitored by calcium imaging in a Flexstation. For Ca-imaging assays of TRPM8 channel activation, cells were seeded on day 0 at a density of 12000 cells per well in Dulbecco's modified Eagle medium (DMEM) containing 9% foetal bovine serum in black, clear bottom 96-well plates that had been coated with 0.001% polyethyleneimine (molecular weight=60 000, Acros Organics). On day 2, agonists were evaluated via calcium imaging using Fluo-4. Briefly, growth medium was discarded, and the cells were incubated in the dark for 1 h at 37° C. in 50 μL loading buffer consisting of 2.7 μM Fluo-4 AM (Invitrogen) and 2.5 μM probenecid (Sigma-Aldrich) in DMEM (without serum). After incubation, the plates were washed five times with 100 μL of assay buffer (in mM: 130 NaCl, 5 KCl, 10 HEPES, 2 $CaCl_2$, and 10 glucose, pH7.4.) and further incubated in the dark at room temperature for 30 min. The cells were then washed five times with 100 μL assay buffer and then calcium influx to serial dilutions of inventive compounds were measured in a Flexstation 3 (Molecular Devices). Receptor activation was initiated following addition of 20 μl of a 10-fold concentrated ligand stock solution, which is also prepared in assay buffer. Fluorescence was continuously monitored for 15 seconds prior to ligand addition and for 105 seconds after ligand addition, for a total of 120 seconds. Maximal receptor activation in relation to solvent control and relative to 31.6 μM menthol is determined. Data from serial dilutions were processed with a KNIME workflow to fit a sigmoidal dose-response curve and to extrapolate $EC_{50}$ values.

TRPM8 agonist exhibiting an $EC_{50}$ value below 35 μM are presented in Table 1 below.

TABLE 1

| Chemical Name | EC50 |
|---|---|
| 1-(2-(1-propionyl-4-(p-tolyl)-1H-imidazol-2-yl)piperidin-1-yl)propan-1-one | + |
| 1-(2-(1-isobutyryl-4-(p-tolyl)-1H-imidazol-2-yl)piperidin-1-yl)-2-methylpropan-1-one | +++ |
| 2-(methylthio)-1-(2-(1-(2-(methylthio)propanoyl)-4-(p-tolyl)-1H-imidazol-2-yl)piperidin-1-yl)propan-1-one | ++++ |
| 1-(2-(1-acetyl-4-(p-tolyl)-1H-imidazol-2-yl)piperidin-1-yl)-2-(methylthio)propan-1-one | +++ |
| 1-(2-(1-isobutyryl-4-(p-tolyl)-1H-imidazol-2-yl)piperidin-1-yl)-2-(methylthio)propan-1-one | ++++ |
| 1-(2-(1-benzoyl-4-(p-tolyl)-1H-imidazol-2-yl)piperidin-1-yl)-2-(methylthio)propan-1-one | ++++ |
| 1-(2-(1-((1R,2S,5R)-2-isopropyl-5-methylcyclohexane-1-carbonyl)-4-(p-tolyl)-1H-imidazol-2-yl)piperidin-1-yl)-2-(methylthio)propan-1-one | ++ |
| 1-(2-(1-acetyl-4-(p-tolyl)-1H-imidazol-2-yl)piperidin-1-yl)-2-methylbutan-1-one | ++++ |
| 1-(2-(1-isobutyryl-4-(p-tolyl)-1H-imidazol-2-yl)piperidin-1-yl)-2-methylbutan-1-one | +++ |
| 1-(2-(1-((1R,2S,5R)-2-isopropyl-5-methylcyclohexane-1-carbonyl)-4-(p-tolyl)-1H-imidazol-2-yl)piperidin-1-yl)-2-methylbutan-1-one | + |
| 1-(2-(1-(2-methoxyacetyl)-4-(p-tolyl)-1H-imidazol-2-yl)piperidin-1-yl)-2-methylbutan-1-one | ++++ |
| 1-(2-(1-(2-(benzyloxy)acetyl)-4-(p-tolyl)-1H-imidazol-2-yl)piperidin-1-yl)-2-methylbutan-1-one | ++++ |
| 1-(2-(1-(2-(methylthio)propanoyl)piperidin-2-yl)-4-(p-tolyl)-1H-imidazol-1-yl)dodecan-1-one | +++ |
| 1-(2-(1-(2-methylbutanoyl)piperidin-2-yl)-4-(p-tolyl)-1H-imidazol-1-yl)dodecan-1-one | ++ |
| 1-(2-(1-(2-(methylthio)propanoyl)piperidin-2-yl)-4-(p-tolyl)-1H-imidazol-1-yl)hexan-1-one | +++ |
| 1-(2-(1-(2-methylbutanoyl)piperidin-2-yl)-4-(p-tolyl)-1H-imidazol-1-yl)hexan-1-one | ++++ |
| N-(1-benzoyl-1H-pyrazol-3-yl)-N-(thiophen-2-ylmethyl)-2-(p-tolyloxy)acetamide | ++++ |

TABLE 1-continued

| Chemical Name | EC50 |
|---|---|
| N-(1-isobutyryl-1H-pyrazol-3-yl)-N-(thiophen-2-ylmethyl)-2-(p-tolyloxy)acetamide | ++++ |
| N-(1-acetyl-1H-pyrazol-3-yl)-N-(thiophen-2-ylmethyl)-2-(p-tolyloxy) acetamide | ++++ |

++++ $EC_{50}$ Value in the range of 0.05 μM and lower
+++ $EC_{50}$ value in the range of 0.05-0.3 μM
++ $EC_{50}$ value in the range of 0.3-1.00 μM
+ $EC_{50}$ value in the range of 1.00-35 μM

The invention claimed is:

1. A method of modulating of transient receptor potential channel melastatin member 8 (TRPM8) comprising bringing the receptor into contact with a compound of formula (I), a salt or solvate thereof (I)

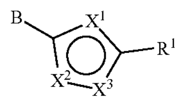

wherein one of $X^1$, $X^2$, and $X^3$ is >N—C (O) R and the other two are independently selected from C, N, and O, with the proviso that not both of them are C, and wherein R is selected from $C_1$-$C_{15}$ hydrocarbon residue optionally comprising one heteroatom selected from O and S; and a) R1 is H; and B represents a monovalent residue (a)

(a)

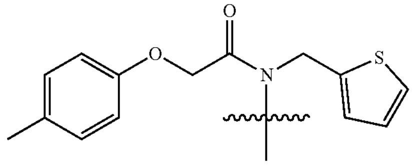

or b) $R^1$ is selected from i) halogen, ii) $C_6$-$C_{10}$ aryl optionally substituted with up to four substituents independently selected from the group consisting of:

halogen; OH (hydroxyl); C≡N (cyano); $NO_2$ (nitro);

$C_1$-$C_6$ alky optionally comprising up to 5 halogen atoms;

$C_1$-$C_3$ alkyl comprising up to 3 OH groups;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—C(O) $R^{10}$ wherein $R^{10}$ is selected from $C_1$-$C_3$ alkyl;

—OC(O) $R^{11}$ wherein $R^{11}$ is selected from H, and $C_1$-$C_3$ alkyl;

—C(O) O—$R^{12}$ wherein $R^{12}$ is selected from hydrogen and $C_1$-$C_3$ alkyl;

—$(CH_2)_m$N $(R^{13})R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxothiomorpholine;

—$SR^{17}$ wherein $R^{17}$ is selected from hydrogen and $C_1$-$C_3$ alkyl; and —$S(O)_2R^{18}$ wherein $R^{18}$ is selected from hydrogen and $C_1$-$C_3$ alkyl;

with the proviso that when the aryl ring is substituted with two or more substituents, two substituents may form a cyclic ring together with the carbon atoms to which they are attached, and iii) $C_5$-$C_{10}$ mono- or bicyclic heteroaryl wherein up to 2 C-atoms are replaced by a hetero atoms independently selected from sulfur, nitrogen, and oxygen, optionally substituted with up to four substituents selected from the group consisting of halogen; OH; C≡N; $NO_2$;

$C_1$-$C_6$ alky optionally comprising up to 5 halogen atoms;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—$C(O)R^{20}$ wherein $R^{20}$ is selected from $C_1$-$C_3$ alkyl;

—$OC(O)R^{21}$ wherein $R^{21}$ is selected from H, and $C_1$-$C_3$ alkyl;

—C(O)O-$R^{22}$ wherein $R^{22}$ is selected from hydrogen and $C_1$-$C_3$ alkyl;

—$(CH_2)_m$N$(R^{23})R^{24}$ wherein m is 0 or 1, $R^{23}$ is selected from hydrogen, $C_1$-$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxothiomorpholine;

—$SR^{27}$ wherein $R^{27}$ is selected from hydrogen and $C_1$-$C_3$ alkyl; and —$S(O)_2R^{28}$ wherein $R^{28}$ is selected from hydrogen and $C_1$-$C_3$ alkyl; and B represents a monovalent residue (b)

(b)

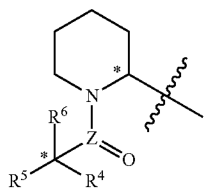

wherein $R^4$, $R^5$ and $R^6$ form together with the carbon atom to which they are attached a hydrocarbon group optionally comprising up to five hetero atoms selected from O, N, S, and F; and Z is either C, S or S(O).

2. The method according to claim 1 wherein the compound of formula (I) is selected from the group consisting of 1-(2-(1-propionyl-4-(p-tolyl)-1H- imidazol-2-yl) piperidin-1-yl) propan-1-one; 1-(2-(1-isobutyryl-4-(p-tolyl)-1H-imidazol-2-y1) piperidin-1-yl)-2-methylpropan-1-one; 2-(methylthio)-1-(2-(1-(2-(methylthio) propanoyl) -4-(p-tolyl)-1H-imidazol-2-yl) piperidin-1-yl) propan-1-one; 1-(2-(1-acetyl-4-(p-tolyl)-1H -imidazol-2-yl) piperidin-1-yl)-2-(methylthio) propan-1-one; 1-(2-(1-isobutyryl-4-(p-tolyl) -1H-imidazol-2-yl) piperidin-1-yl)-2-(methylthio) propan-1-one; 1-(2-(1-benzoyl-4-(p-tolyl) -1H-imidazol-2-yl) piperidin-1-yl)-2-(methylthio) propan-1-one; 1-(2-(1- ((1R,2S,5R)-2-isopropyl-5-methylcyclohexane-1-carbonyl)-4-(p-tolyl)-1H-imidazol-2-yl) piperidin-1-yl)-2-(methylthio) propan-1-one; 1-(2-(1-acetyl-4-(p-tolyl)-1H-imidazol-2-yl) piperidin-1-yl)-2-methylbutan-1-one; 1-(2-(1-isobutyryl-4-(p-tolyl)-1H-imidazol-2-yl) piperidin-1-yl)-2-methylbutan-1-one; 1-(2-(1- ((1R,2S,5R)-2-isopropyl-5-methylcyclohexane-1-carbonyl)-4-(p-tolyl)-1H-imidazol-2-yl) piperidin-1-yl)-2-methylbutan-1-one; 1-(2-(1-(2-methoxyacetyl) -4-(p-tolyl)-1H-imidazol-2-yl) piperidin-1-yl)-2-methylbutan-1-one; 1-(2-(1-(2-(benzyloxy) acetyl)-4-(p-tolyl)-1H-imidazol-2-yl) piperidin-1-yl)-2-methylbutan-1-one; 1-(2-(1-(2-(methylthio) propanoyl) piperidin-2-yl)-4-(p-tolyl)-1H-imidazol-1-yl) dodecan-1-one; 1-(2-(1-(2-methylbutanoyl) piperidin-2-yl)-4-(p-tolyl)-1H-imidazol-1-yl) dodecan-1-one; 1-(2-(1-(2-(methylthio) propanoyl) piperidin-2-yl)-4-(p-tolyl)-1H-imidazol-1-yl) hexan-1-one; 1-(2-(1-(2-methylbutanoyl) piperidin-2-yl)-4-(p-tolyl)-1H-imidazol-1-yl) hexan-1-one; N-(1-benzoyl-1H-pyrazol-3-yl)-N-(thiophen-2-ylmethyl)-2-(p-tolyloxy) acetamide; N-(1-isobutyryl-1H-pyrazol-3-yl)-N-(thiophen-2-ylmethyl)-2-(p-tolyloxy) acetamide; N-(1-acetyl-1H-pyrazol-3-yl)-N-(thiophen-2-ylmethyl)-2-(p-tolyloxy) acetamide, and combinations thereof.

3. A non-medical method of inducing a cooling sensation in a human or animal comprising contacting the human or animal with a compound of formula (I), or a salt or solvate thereof, as defined in claim 1.

4. A method of achieving a cooling effect on the skin or mucosa comprising contacting the skin or mucosa with a product comprising one or more compounds of formula (I) as defined in claim 1.

5. A compound of formula (I), a salt or solvate thereof (I)

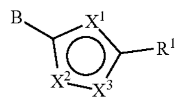

wherein one of $X^1$, $X^2$, and $X^3$ is >N—C(O)R and the other two are independently selected from C, N, and O, with the proviso that not both of them are C, and wherein R is selected from $C_1$-$C_{15}$ hydrocarbon residue optionally comprising one heteroatom selected from O and S; and a) $R^1$ is H; and B represents a monovalent residue (a)

(a)

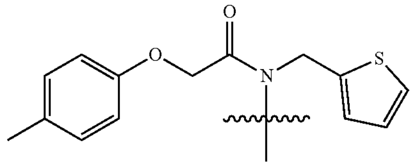

or b) $R^1$ is selected from i) halogen, ii) $C_6$-$C_{10}$ aryl optionally substituted with up to four substituents independently selected from the group consisting of:

halogen; OH (hydroxyl); C≡N (cyano); $NO_2$ (nitro);

$C_1$-$C_6$ alky optionally comprising up to 5 halogen atoms;

$C_1$-$C_3$ alkyl comprising up to 3 OH groups;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—C(O)$R^{10}$ wherein $R^{10}$ is selected from $C_1$-$C_3$ alkyl;

—OC(O)$R^{11}$ wherein $R^{11}$ is selected from H, and $C_1$-$C_3$ alkyl;

—C(O)O—$R^{12}$ wherein $R^{12}$ is selected from hydrogen and $C_1$-$C_3$ alkyl;

—$(CH_2)_m$N($R^{13}$)$R^{14}$ wherein m is 0 or 1, $R^{13}$ is selected from hydrogen, $C_1$-$C_3$ alkyl, and —$SO_2R^{15}$ wherein $R^{15}$ is $C_1$-$C_3$ alkyl, and $R^{14}$ is selected from hydrogen, $C_1$-$C_3$ alkyl, and —$SO_2R^{16}$ wherein $R^{16}$ is $C_1$-$C_3$ alkyl, or wherein $R^{13}$ and $R^{14}$ form together with the N atom to which they are attached morpholine, thiomorpholine, or 1,1-dioxothiomorpholine;

—$SR^{17}$ wherein $R^{17}$ is selected from hydrogen and $C_1$-$C_3$ alkyl; and —$S(O)_2R^{18}$ wherein $R^{18}$ is selected from hydrogen and $C_1$-$C_3$ alkyl;

with the proviso that when the aryl ring is substituted with two or more substituents, two substituents may form a cyclic ring together with the carbon atoms to which they are attached, and iii) $C_5$-$C_{10}$ mono-or bicyclic heteroaryl wherein up to 2 C-atoms are replaced by a hetero atoms independently selected from sulfur, nitrogen, and oxygen, optionally substituted with up to four substituents selected from the group consisting of halogen; OH; C≡N; $NO_2$;

$C_1$-$C_6$ alky optionally comprising up to 5 halogen atoms;

$C_1$-$C_3$ alkyl comprising up to 3 OH groups;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—C(O)$R^{20}$ wherein $R^{20}$ is selected from $C_1$-$C_3$ alkyl;

—OC(O) $R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl;

—$(CH_2)_m$N($R^{23}$)$R^{24}$ wherein m is 0 or 1, $R^{23}$ is selected from hydrogen, $C_1$-$C_3$ alkyl, and —$SO_2R^{25}$ wherein $R^{25}$ is $C_1$-$C_3$ alkyl, and $R^{24}$ is selected from hydrogen, $C_1$-$C_3$ alkyl, and —$SO_2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxothiomorpholine;

—$SR^{27}$ wherein $R^{27}$ is selected from hydrogen and $C_1$-$C_3$ alkyl; and —$S(O)_2R^{28}$ wherein $R^{28}$ is selected from hydrogen and $C_1$-$C_3$ alkyl; and B represents a monovalent residue (b)

(b)

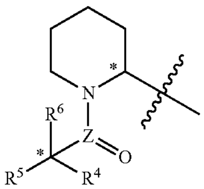

wherein $R^4$, $R^5$ and $R^6$ form together with the carbon atom to which they are attached a hydrocarbon group optionally comprising up to five hetero atoms selected from O, N, S, and F; and Z is either C, S or S(O).

6. A consumer product comprising one or more compounds of formula (I) as defined in claim 5.

7. A pharmaceutical composition comprising one or more compounds of formula (I) as defined in claim 5.

8. A method of utilizing the compound of formula (I) as defined in claim 5 as a medicament for a human or animal comprising contacting the human or animal with one or more compounds of formula (I).

9. A composition comprising at least one compound of formula (I), a salt or solvate thereof, and a further cooling compound.

10. The composition according to claim 9 wherein the further cooling compound from at least one of menthol, menthone, is selected 1 p-menthanecarboxamides, N-2,3-trimethyl-2-isopropyl-butanamide, menthyl lactate, menthone glycerol acetal, 3-(1-menthoxy)-propane-1,2-diol, p-menthane-3,8-diol, isopulegol, monomenthyl succinate, monomenthyl glutarate, o-menthylglycerol, menthyl N,N -dimethylsuccinamate, 2-(sec-butyl) cyclohexan-1-one, N-(pyrazol-3-yl)-N-(thiophen-2-ylmethyl)-2-(p-tolyloxy) acetamide, 2-(4-ethylphenoxy)-N-(pyrazol-3-yl)-N-(thiophen-2-ylmethyl) acetamide, 3-(benzo [d] [1,3] dioxol-5-yl)-N,N-diphenylacrylamide, 4-(2-(4-allyl -2,6-dimethoxyphenoxy)-1-ethoxypropyl)-2-methoxyphenol, 4-(2-(4-allyl-2,6-dimethoxyphenoxy)-1- ((2-isopropyl-5-methylcyclohexyl) oxy) propyl)-2-methoxyphenol, N -(2-Hydroxy-2-phenylethyl)-2-isopropyl-5,5-dimethylcyclohexane-1-carboxamide, N-(4-(Cyanomethyl) phenyl)-2-isopropyl-5,5-dimethylcyclohexanecarboxamide or N-(3-Hydroxy-4-methoxyphenyl)-2-isopropyl-5,5-dimethylcyclohexanecarboxamide.

11. A method of achieving a cooling effect on the skin or mucosa comprising hydrolysing the acetyl group (>N—C (O) R) of the compound of formula (I) as defined in claim 1, resulting in a compound of formula (I') and contacting the skin or mucosa with a compound of formula (I'), or a salt or solvate thereof (I')

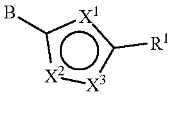

wherein one of $X^1$, $X^2$, and $X^3$ is >NH and the other two are independently selected from C, N, and O, with the proviso that not both of them are C; and a) $R^1$ is H; and B represents a monovalent residue (a)

(a)

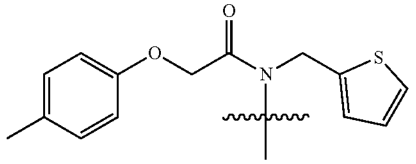

or b) R1 is selected from i) halogen, ii) C6-C10 aryl optionally substituted with up to four substituents independently selected from the group consisting of:

halogen; OH (hydroxyl); C≡N (cyano); $NO_2$ (nitro);

$C_1$-$C_6$ alky optionally comprising up to 5 halogen atoms;

$C_1$-$C_3$ alkyl comprising up to 3 OH groups;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—C(O) $R^{10}$ wherein $R^{10}$ is selected from $C_1$-$C_3$ alkyl;

—OC(O) $R^{11}$ wherein $R^{11}$ is selected from H, and $C_1$-$C_3$ alkyl;

—C(O) O-$R^{12}$ wherein $R^{12}$ is selected from hydrogen and $C_1$-$C_3$ alkyl;

—$(CH_2)_m N(R^{13})R^{14}$ wherein m is 0 or 1, $R^{13}$ is selected from hydrogen, C1-C3 alkyl, and —$SO_2R^{15}$ wherein R15 is C1-C3 alkyl, and $R^{14}$ is selected from hydrogen, $C_1$-$C_3$ alkyl, and —$SO_2R^{16}$ wherein R16 is C1-C3 alkyl, or wherein $R^{13}$ and $R^{14}$ form together with the N atom to which they are attached morpholine, thiomorpholine, or 1,1-dioxo-thiomorpholine;

—$SR^{17}$ wherein $R^{17}$ is selected from hydrogen and $C_1$-$C_3$ alkyl; and —$S(O)_2R^{18}$ wherein $R^{18}$ is selected from hydrogen and $C_1$-$C_3$ alkyl;

with the proviso that when the aryl ring is substituted with two or more substituents, two substituents may form a cyclic ring together with the carbon atoms to which they are attached, and iii) $C_5$-$C_{10}$ mono-or bicyclic heteroaryl wherein up to 2 C-atoms are replaced by a hetero atoms independently selected from sulfur, nitrogen, and oxygen, optionally substituted with up to four substituents selected from the group consisting of halogen; OH; C≡N; $NO_2$;

$C_1$-$C_6$ alky optionally comprising up to 5 halogen atoms;

$C_1$-$C_3$ alkyl comprising up to 3 OH groups;

$C_2$-$C_6$ alkenyl;

$C_1$-$C_6$ alkoxy optionally comprising up to 3 halogen atoms;

$C_1$-$C_3$ alkoxy $C_1$-$C_3$ alkyl;

$C_3$-$C_7$ cycloalkyl;

—C(O)$R^{20}$ wherein $R^{20}$ is selected from $C_1$-$C_3$ alkyl;

—OC(O)$R^{21}$ wherein $R^{21}$ is selected from H, and $C_1$-$C_3$ alkyl;

—C(O)O—$R^{22}$ wherein $R^{22}$ is selected from hydrogen and $C_1$-$C_3$ alkyl;

—$(CH_2)_m N(R^{23})R^{24}$ wherein m is 0 or 1, $R^{23}$ is selected from hydrogen, $C_1$-$C_3$ alkyl, and —$SO^2R^{25}$ wherein $R^{25}$ is $C_1$-$C_3$ alkyl, and $R^{24}$ is selected from hydrogen, $C_1$-$C_3$ alkyl, and —$SO^2R^{26}$ wherein $R^{26}$ is $C_1$-$C_3$ alkyl, or wherein $R^{23}$ and $R^{24}$ form together with the N atom to which they are attached morpholine, thiomorpholine, or 1,1-dioxothiomorpholine;

—$SR^{27}$ wherein $R^{27}$ is selected from hydrogen and $C_1$-$C_3$ alkyl; and —$S(O)^2R^{28}$ wherein R28 is selected from hydrogen and $C_1$-$C_3$ alkyl;

and

B represents a monovalent residue (b)

(b)

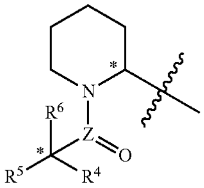

wherein $R^4$, $R^5$ and $R^6$ form together with the carbon atom to which they are attached a hydrocarbon group optionally comprising up to five hetero atoms selected from O, N, S, and F; and Z is either C, S or S (O).

12. The composition according to claim 10, wherein the composition is a mediator of the transient receptor potential channel melastatin member 8 (TRPM8) and is selected from the group consisting of food products, beverages, chewing gum, tobacco and tobacco replacement products, dental care products, personal care products, intimate care products and combinations thereof.

13. The composition according to claim 9, wherein the composition is a mediator of the transient receptor potential channel melastatin member 8 (TRPM8) and is selected from the group consisting of food products, beverages, chewing gum, tobacco and tobacco replacement products, dental care products, personal care products, intimate care products and combinations thereof.

14. The composition according to claim 10, wherein the composition is a mediator of the transient receptor potential channel melastatin member 8 (TRPM8) and is selected from the group consisting of food products, beverages, chewing gum, tobacco and tobacco replacement products, dental care products, personal care products, intimate care products and combinations thereof.

* * * * *